(12) United States Patent
Tuemmler et al.

(10) Patent No.: US 7,702,477 B2
(45) Date of Patent: Apr. 20, 2010

(54) CALIBRATION METHOD AND CALIBRATION DEVICE FOR A SURGICAL REFERENCING UNIT

(75) Inventors: Hanns-Peter Tuemmler, Tuttlingen (DE); Andreas Goeggelmann, Ingersheim (DE); Dieter Mintenbeck, VS-Rietheim (DE); Thomas Link, Rottweil (DE)

(73) Assignee: Aesculap AG, Tuttlingen (DE)

( * ) Notice: Subject to any disclaimer, the term of this patent is extended or adjusted under 35 U.S.C. 154(b) by 330 days.

(21) Appl. No.: 11/824,487

(22) Filed: Jun. 28, 2007

(65) Prior Publication Data

US 2008/0039868 A1   Feb. 14, 2008

(30) Foreign Application Priority Data

Jul. 5, 2006   (DE) ........................ 10 2006 032 127

(51) Int. Cl.
*G01C 17/38* (2006.01)
*A61B 19/00* (2006.01)

(52) U.S. Cl. ........................................ 702/95; 606/130
(58) Field of Classification Search .................. 702/89, 702/95; 606/100, 130; 600/424
See application file for complete search history.

(56) References Cited

U.S. PATENT DOCUMENTS

| | | | |
|---|---|---|---|
| 3,983,474 A | 9/1976 | Kuipers | |
| 4,054,881 A | 10/1977 | Raab | |
| 4,912,643 A | 3/1990 | Beirxe | |
| 5,396,510 A | 3/1995 | Wilson | |
| 5,452,211 A | 9/1995 | Kyrtsos et al. | |
| 5,617,857 A | 4/1997 | Chader et al. | |
| 5,645,077 A | 7/1997 | Foxlin | |
| 5,676,157 A | 10/1997 | Kramer | |
| 5,854,843 A | 12/1998 | Jacknin et al. | |
| 5,921,992 A | 7/1999 | Costales et al. | |
| 5,953,683 A | 9/1999 | Hansen et al. | |
| 6,044,297 A | 3/2000 | Sheldon et al. | |
| 6,306,126 B1 | 10/2001 | Moctezuma | |
| 6,988,009 B2 | 1/2006 | Grimm et al. | |
| 2003/0209096 A1* | 11/2003 | Pandey et al. ............... | 73/865.9 |
| 2004/0039402 A1 | 2/2004 | Zeiss et al. | |
| 2004/0149036 A1 | 8/2004 | Foxlin et al. | |
| 2004/0201857 A1 | 10/2004 | Foxlin | |

FOREIGN PATENT DOCUMENTS

| | | |
|---|---|---|
| DE | 34 06 179 | 9/1985 |
| DE | 35 27 918 | 2/1987 |
| DE | 36 01 536 | 7/1987 |
| DE | 40 27 990 | 2/1992 |
| DE | 44 34 666 | 4/1995 |
| DE | 44 11 218 | 9/1995 |
| DE | 44 15 419 | 11/1995 |
| DE | 44 22 886 | 1/1996 |
| DE | 196 32 273 | 2/1998 |
| DE | 198 30 359 | 1/2000 |
| DE | 199 06 094 | 9/2000 |

(Continued)

*Primary Examiner*—Bryan Bui
(74) *Attorney, Agent, or Firm*—Lipsitz & McAllister, LLC

(57) ABSTRACT

A calibration method and also a calibration device are proposed to enable a spatial position and/or orientation of a surgical referencing unit of a surgical navigation system fitted with at least one inertial sensor to be specified in relation to a spatial coordinate system.

63 Claims, 12 Drawing Sheets

FOREIGN PATENT DOCUMENTS

| | | |
|---|---|---|
| DE | 100 45 381 | 4/2002 |
| DE | 103 12 154 | 6/2004 |
| DE | 10 2004 048 066 | 4/2006 |
| DE | 10 2004 057 933 | 6/2006 |
| EP | 0 211 984 | 9/1996 |
| EP | 0 986 991 | 3/2000 |
| EP | 1 460 378 | 9/2004 |
| EP | 1 280 457 | 11/2005 |
| WO | 94/01042 | 1/1994 |
| WO | 96/11624 | 4/1996 |
| WO | 01/67979 | 9/2001 |
| WO | 02/061371 | 8/2002 |
| WO | 2006/029541 | 3/2006 |

* cited by examiner

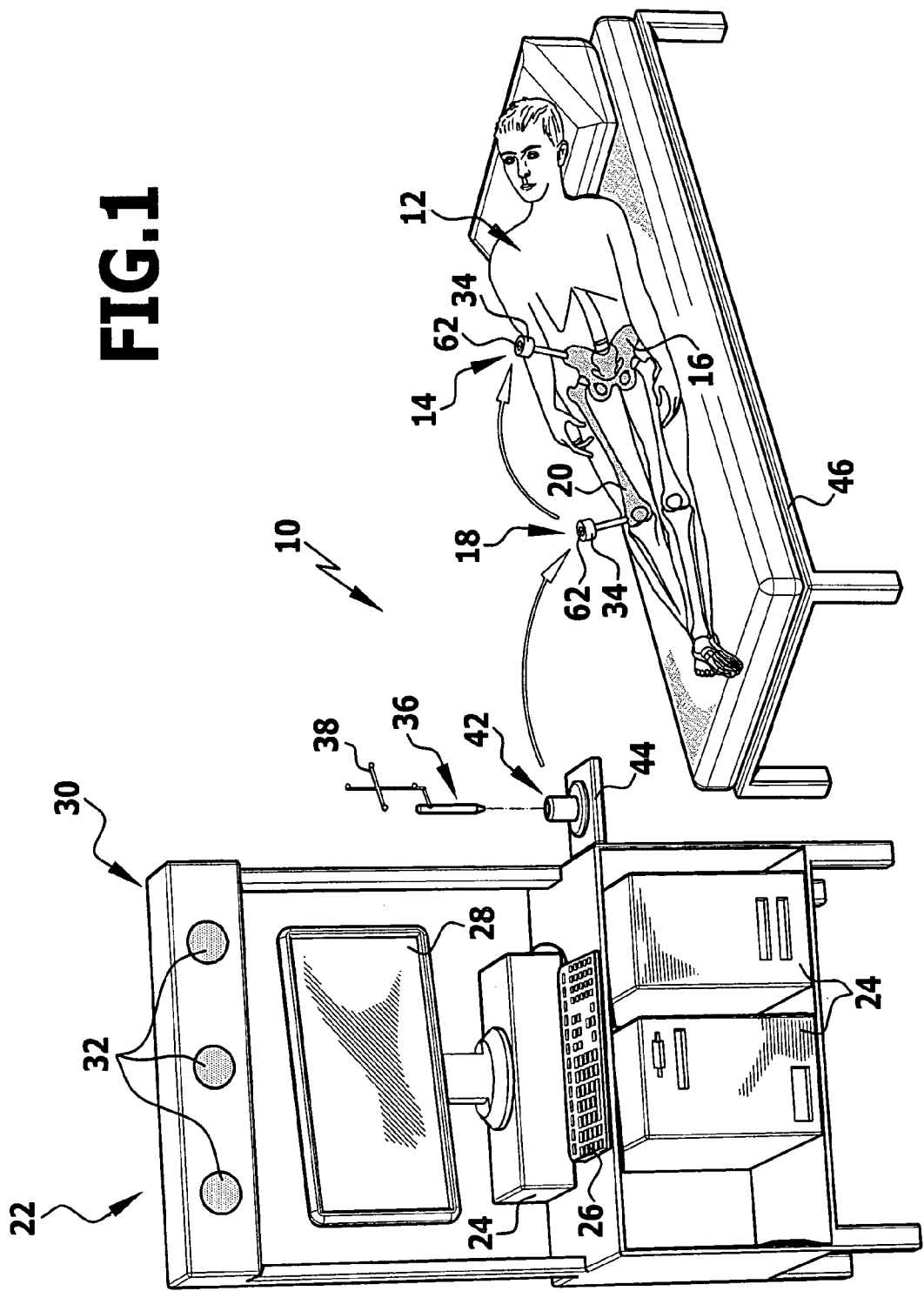

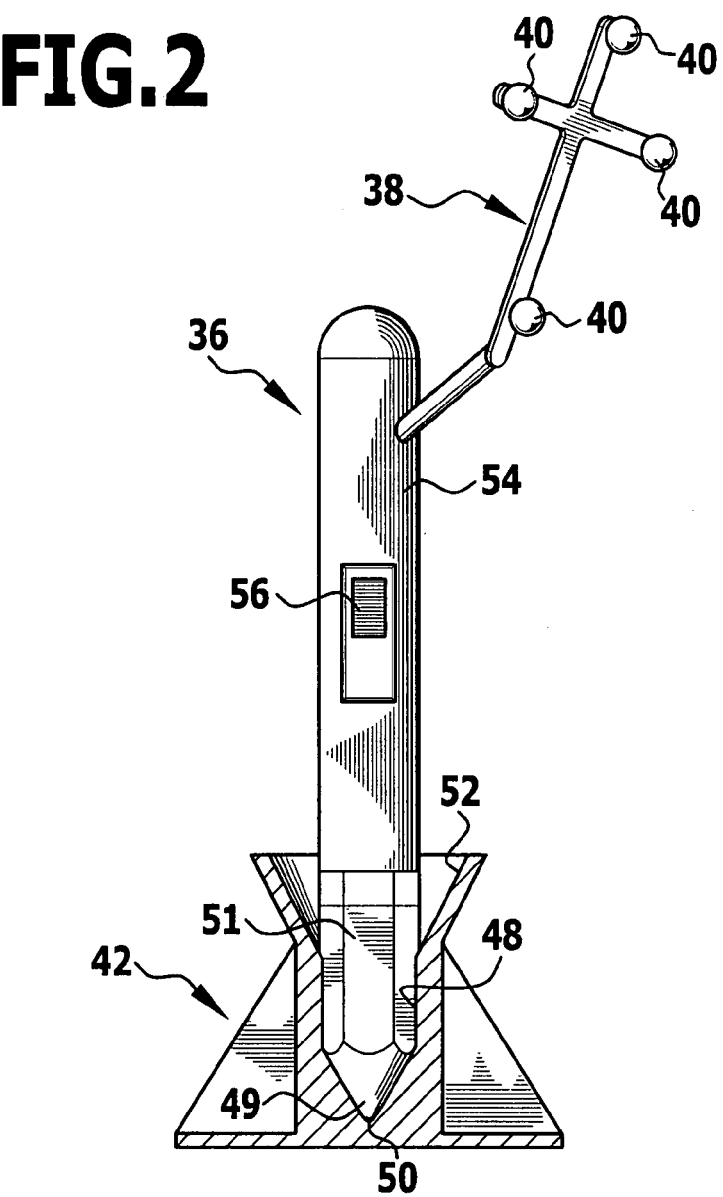
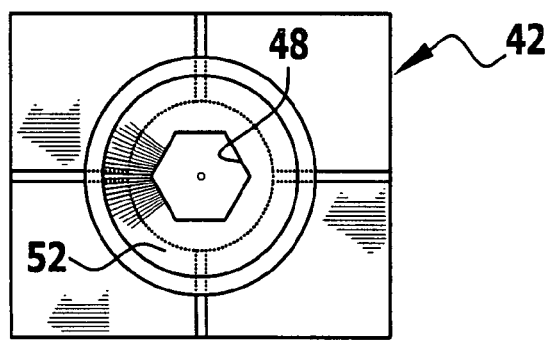

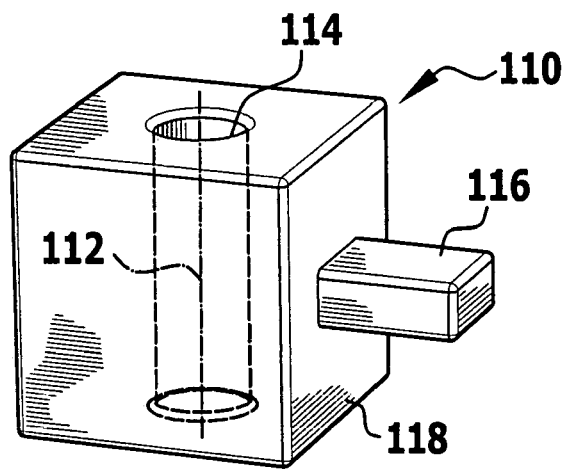
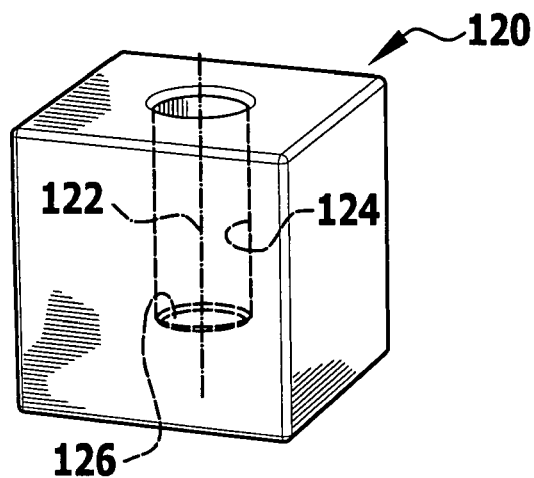
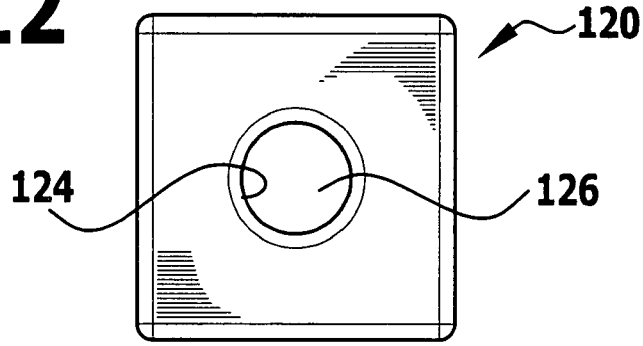

CALIBRATION METHOD AND CALIBRATION DEVICE FOR A SURGICAL REFERENCING UNIT

The present disclosure relates to the subject matter disclosed in German application number 10 2006 032 127.8 filed Jul. 5, 2006, which is incorporated herein by reference and in its entirety and for all purposes.

BACKGROUND OF THE INVENTION

The present invention relates to a method for calibrating a spatial position and/or orientation of at least one surgical referencing unit of a surgical navigation system fitted with at least one inertial sensor in relation to a spatial coordinate system.

The present invention also relates to a surgical calibration device for calibrating a spatial position and/or orientation of at least one surgical referencing unit of a surgical navigation system fitted with at least one inertial sensor in relation to a spatial coordinate system.

Known surgical navigation systems comprise referencing units that either reflect electromagnetic radiation emitted by a detection device of the navigation system or themselves emit electromagnetic radiation that can be received by the detection device. In alternative embodiments, it is also known to use ultrasound instead of electromagnetic radiation. A spatial position of the referencing unit can be determined absolutely in relation to a coordinate system defined by the detection device by means of transit-time measurements with navigation systems based on ultrasound that is emitted and received again by the detection device. A determination of position and/or orientation with navigation systems emitting and/or receiving electromagnetic radiation is based on field changes. Moreover, it is also possible to detect position or orientation changes by purely video-optical means. Navigation systems that perform a position and/or orientation detection purely by means of imaging processes are used for this purpose.

The aim of using a navigation system is to track spatial movements of the referencing units. As described above, absolute position data and/or orientations of the referencing unit can be determined by means of known navigation systems for this purpose. A movement path of the referencing unit can be reconstructed or computed on the basis of the determined position data and/or orientations.

However, if a surgical referencing unit is fitted with at least one inertial sensor, then a determination of position and/or orientation data of the referencing unit in any desired coordinate system can no longer occur directly, but must be computed on the basis of position and/or orientation changes. The reason for this, amongst other things, is that inertial sensors are sensors, with which forces and/or accelerations acting on them as a result of position and/or orientation changes can be measured. If more than one inertial sensor is used, in particular when six inertial sensors are used, three of which can detect the forces and/or accelerations in three mutually linearly independent directions and three of which can detect rotational angle changes around three mutually linearly independent axes, then position and/or orientation changes can also be determined uniquely in three-dimensional space on the basis of forces and/or accelerations acting on the inertial sensors.

Since no absolute position and/or orientation data can be determined directly with inertial sensors, it is therefore an object of the present invention to propose a method and a device of the above-described type, with which it is possible to reference or calibrate the at least one referencing unit in a predefined spatial coordinate system.

SUMMARY OF THE INVENTION

This object is achieved according to the invention by a method of the above-described type, comprising:
providing a calibration unit, the position and/or orientation data of which are determinable in relation to the coordinate system by the navigation system;
bringing the calibration unit and the at least one referencing unit into a one-to-one calibration position relative to one another, in which the calibration unit and the at least one referencing unit respectively assume a defined calibration position and/or orientation relative to one another;
determining calibration position and/or orientation data of the calibration unit in the calibration position by means of the navigation system;
calculating calibration position and/or orientation data of the referencing unit in the calibration position on the basis of the calibration position and/or orientation data of the calibration unit, and
assigning the calibration position and/or orientation data calculated for the at least one referencing unit in the calibration position to the at least one referencing unit.

The method according to the invention enables position and/or orientation data relative to the coordinate system to be assigned to the at least one referencing unit. Position and/or orientation changes that result because of forces and/or accelerations acting on the at least one inertial sensor can therefore be determined in a simple manner in relation to the spatial coordinate system. The proposed method is simple to perform, since the calibration unit, the spatial position and/or orientation of which is determinable by the navigation system, serves to calibrate the at least one referencing unit. For this, the method provides in particular that the at least one referencing unit and the calibration unit are brought into a one-to-one calibration position relative to one another and then position and/or orientation data are assigned to the at least one referencing unit, in particular on the basis of determined calibration position and/or orientation data of the calibration unit in the calibration position that can be determined, for example, by means of the navigation system. These data, or also position and/or orientation data that result on the basis of the one-to-one relative position of the at least one referencing unit and the calibration unit in the calibration position, can be assigned directly to the at least one referencing unit. The method according to the invention is eminently suitable for a quick and simple calibration or referencing of the at least one referencing unit. In particular, the proposed calibration method can be repeated as frequently as desired. A multiple referencing or calibration of the at least one referencing unit may be necessary in the case of standard inertial sensors, since these have a time-dependent drift, and therefore inaccuracies with respect to forces and/or accelerations acting on the inertial sensors can occur, particularly in the case of long-term measurements, and consequently inaccuracies can then also result in the determination of position and/or orientation data. Moreover, supplementary calibrations and/or referencing may be necessary if the at least one referencing unit is only subjected to small position changes.

It is advantageous if a non-fixed coordinate system is predefined as coordinate system, and if an origin of the non-fixed coordinate system is predefined by the calibration position and/or orientation data of the at least one referencing unit or the calibration unit in the calibration position. Non-fixed for the purpose of this application means, in particular, non-stationary. While no absolute spatial position and/or orientation data can be determined by the non-fixed coordinate system, relative positions in particular with respect to the origin of the non-fixed coordinate system are determined. This method is particularly simple, is associated with a reduced computational effort and is particularly suitable for cases, in which absolute referencing in a fixed coordinate system, e.g. an operating theatre, is not essential.

Moreover, it can be favourable when at least two referencing units are calibrated, if a non-fixed coordinate system is predefined as coordinate system, and if an origin of the non-fixed coordinate system is predefined by one of the at least two referencing units. Position and/or orientation changes can then be determined in a simple manner in relation to one of the at least two referencing units. This method can be used advantageously in particular when no absolute referencing is required in a coordinate system relating to an operating theatre, for example.

If, for example, referencing in relation to a fixed coordinate system, e.g. relating to an operating theatre, for example, is desired, it is advantageous if a spatially fixed origin of an absolute coordinate system is predefined, if the calibration unit is brought into an origin calibration position, in which the calibration unit is positioned in a defined relation to the fixed origin, and if origin position and/or orientation data of the calibration unit in the origin calibration position relative to the fixed origin are assigned to the calibration unit. This procedure allows in particular referencing units fitted with at least one inertial sensor together with referencing units, which emit and/or reflect electromagnetic radiation and are not fitted with inertial sensors or which can be navigated by means of ultrasound or by video-optical means, to be used by navigation systems described above and in association with such navigation systems.

To enable calibration or referencing to be performed automatically by means of the navigation system or parts thereof, it is favourable if a calibration signal is generated when the calibration unit and the at least one referencing unit assume the calibration position. The calibration signal then indicates when the calibration unit and the at least one referencing unit assume the position, in which a calibration or referencing is to be performed.

According to a preferred variant of the method according to the invention it is favourable if the calibration signal is only generated after a holding time $t_H$, during which the calibration unit and the at least one referencing unit assume the calibration position without or substantially without any relative movement. Thus, calibration or referencing errors can be minimised or often even completely excluded.

It is favourable if an actuating element is actuated in the calibration position, and if the calibration signal is only generated during or as a consequence of an actuation of the actuating element. In this way, it can be ensured in particular that a calibration signal is generated only upon specific actuation of the actuating element. This can be generated, for example, by simple actuation of the actuating element, i.e. during actuation and/or release of the actuating element. It would also be conceivable for the calibration signal to only be generated when the actuating element has been permanently actuated during a predefined or predefinable actuation time.

The actuating element is advantageously actuated by means of the calibration unit and/or the at least one referencing unit. Thus, it is possible in particular that the actuating element is actuated automatically in the calibration position by the calibration unit or the at least one referencing unit. For example, the actuating element could be arranged on the calibration unit and/or the at least one referencing unit.

In principle, it would be possible to use an optical or acoustic switching element as actuating element. Proximity switches of inductive or capacitive design would also be possible. A calibration signal can be generated in a particularly simple and defined manner by actuating the actuating element if a mechanical switch, particularly in the form of a key, hand switch or foot switch, is used as actuating element. If the actuating element is not arranged on the calibration unit and not arranged in the at least one referencing unit, these two units can be configured to be particularly small. In particular, it would also be possible by separating the actuating element and calibration unit or referencing unit, even by spatially separating these, for example, to enable the actuating element to be actuated by a person who is not present in an operating theatre, for example. In this way, non-sterilisable actuating elements can also be used.

It is advantageous if only after the calibration signal is present, the calibration position and/or orientation data in the calibration position of the navigation system are determined, the calibration position and/or orientation data of the at least one referencing unit in the calibration position are calculated and the calibration position and/or orientation data calculated for the at least one referencing unit in the calibration position are assigned to the at least one referencing unit. This procedure enables accuracy of the calibration method to be significantly increased, in particular when the calibration signal is only generated when the calibration unit and the at least one referencing unit assume the calibration position.

Advantageously, an origin calibration signal is generated when the calibration unit assumes the origin calibration position. Thus, position and/or orientation data of an origin, for example, of a fixed coordinate system can be assigned to the calibration unit in a defined manner.

In order to increase the accuracy of a referencing or calibration of the calibration unit relative to the origin, it is advantageous if the origin calibration signal is only generated after a holding time $t_{H\_origin}$, during which the calibration unit assumes the origin calibration position without movement or substantially without movement.

According to a preferred variant of the method of the invention it can be provided that in the origin calibration position an origin calibration actuating element is actuated, and that the origin calibration signal is only generated during or as a consequence of an actuation of the origin calibration actuating element. An automatic referencing or calibration of the calibration unit relative to the origin can occur in particular in this way.

For an automatic initialisation of the calibration method, it is favourable if the origin calibration actuating element is actuated by the calibration unit or a referencing device. A device, in relation to which the calibration unit can be brought into a defined origin calibration position, for example, can serve as referencing device. For example, the referencing device can have a receiving means, into which at least a part of the calibration unit in the origin calibration position can engage. It would also be conceivable to use the at least one referencing unit as referencing device.

It would be absolutely possible to use an optical or inductive or capacitive switching element as origin calibration actuating element. However, it is particularly simple if a mechanical switching element, in particular a mechanical key or switch or a foot switch, is used as origin calibration actuating element. In this way, an origin calibration signal can be generated or initialised automatically or purposefully by an operator by means of the origin calibration actuating element.

Advantageously, the origin position and/or orientation data of the calibration unit in the origin calibration position relative to the fixed origin are assigned to the calibration unit only after the origin calibration signal is present. In this way, it can be ensured that a calibration or referencing of the calibration unit relative to the origin only occurs when the calibration unit assumes or has assumed the relative position in relation to the origin necessary for this.

To ensure that false or inaccurate position and/or orientation data of the at least one referencing unit are not determined inadvertently with the navigation system, it is advantageous if a navigation operation of the navigation system is enabled for tracking any movements of the at least one referencing unit only when all referencing units necessary for the navigation operation have been calibrated with the calibration unit in relation to a common coordinate system. Thus, it is ensured in particular that correct position and/or orientation data of the at least one referencing unit are determined by the navigation system.

In order to prevent or at least minimise the determination of inaccurate position and/or orientation data of the at least one referencing unit as well as the calibration unit, it is advantageous if a navigation operation is restricted to a predefinable operating time $t_{operation}$. The operating time can be predefined, for example, in a range of 1 second to 60 minutes, preferably 10 seconds to 20 minutes. The restriction of the navigation operation system to a predefinable operating time in particular prevents inaccuracies in the determination of the position and/or orientation of the at least one referencing unit from occurring as a result of drift of the at least one inertial sensor of the at least one referencing unit after a certain operating time.

Advantageously, the operating time $t_{operation}$ automatically begins to run when all referencing units have been calibrated with the calibration unit in relation to a common coordinate system. In this case, it can also be considered in particular that the operating time $t_{operation}$ begins to run when the first of the referencing units to be calibrated or referenced has been calibrated or referenced.

After expiry of the operating time $t_{operation}$, an optical and/or acoustic warning signal is preferably emitted and/or the navigation operation is automatically terminated. As a result of this, the determination of inaccurate or incorrect values for the position and/or orientation of the at least one referencing unit on the basis of a so-called drifting of the at least one inertial sensor can be prevented.

The method can be performed in a particularly simple and reliable manner if the operating time $t_{operation}$ is monitored by the navigation system.

Depending on the type of inertial sensors used, it is advantageous if the operating time $t_{operation}$ is restricted to a maximum time in the range of 1 second to 60 minutes, preferably in a range of 10 seconds to 20 minutes. In the case of inertial sensors with long-term stability and only very slight drift, the maximum time can even amount to as much as 30 or 40 minutes.

In principle, it would be easily possible to use a calibration unit that is fitted with conventional marker elements, i.e. with marker elements, which either themselves emit electromagnetic radiation that can be received by the detection device of the navigation system, or can react to the electromagnetic radiation emitted by the navigation system. It would naturally also be possible to use a calibration unit that is fitted with marker elements, which can be navigated by navigation systems based on video-optical methods or navigation systems based on ultrasound.

However, it is advantageous if a calibration unit fitted with at least one inertial sensor is provided, the position and/or orientation data of which are determinable in relation to the coordinate system by the navigation system. This allows, for example, the calibration unit and the at least one referencing unit to initialise simultaneously, to "zero" as it were. A calibration of the at least one referencing unit and/or the calibration unit can occur before or after the initialisation. Moreover, the fitting of the calibration unit with at least one inertial sensor has the additional advantage that the navigation system can be provided with a simpler structure overall, since an optical detection device, for example, can then be omitted altogether. Moreover, a detection device that can itself emit radiation in particular can also be omitted. In addition, it would also be possible, if more than one referencing unit is provided to use one of the referencing units themselves as calibration unit.

According to a preferred variant of the method of the invention it can be provided that the calibration unit and the at least one referencing unit respectively have at least one transmitting unit, and that with the at least one transmitting unit changes of the position and/or orientation data of the calibration unit and/or the at least one referencing unit are transmitted to the navigation system or to a detection device thereof. The units thus configured as active referencing units or as active calibration units render an active detection device that can itself emit radiation superfluous. In particular, it would be possible to use transmitting units that emit electromagnetic or infrared radiation, and so-called Bluetooth transmitting units that can communicate in standardised form with a Bluetooth receiving unit of the navigation system are mentioned here by way of example.

For determination of the position and/or orientation data of the calibration unit and the at least one referencing unit, a navigation system is preferably used, which comprises an evaluation unit configured in such a manner that absolute position and/or orientation data can be calculated for the calibration unit and the at least one referencing unit from acceleration values measured by means of the at least one inertial sensor.

The use of such a navigation system has the advantage that a position and/or orientation determination of the calibration unit as well as the at least one referencing unit can be performed fully automatically.

It is favourable if position and/or orientation change data of the calibration unit and the at least one referencing unit are calculated from the measured acceleration values in relation to the coordinate system, and if absolute position and/or orientation data of the calibration unit and the at least one referencing unit are calculated from the calculated position and/or orientation change data in relation to the coordinate system. This procedure has the advantage that when no absolute position and/or change data of the calibration unit and the at least one referencing unit have to be determined, the calculated position and/or orientation change data can be used for a relative position determination. Advantageously, an inertial sensor unit is used as at least one inertial sensor that comprises at least three linear and three rotational acceleration sensors, with which accelerations and/or forces acting on the calibration unit and/or the at least one referencing unit are measured as a function of time in three mutually linearly independent directions and around three mutually linearly independent rotational axes. Such inertial sensor units readily allow all the measured values necessary for a three-dimensional position and/or orientation determination in a coordinate system to be determined.

The aforementioned set object is additionally achieved by a surgical calibration device for calibrating a spatial position and/or orientation of at least one surgical referencing unit of a surgical navigation system fitted with at least one inertial sensor in relation to a spatial coordinate system, comprising:
- a navigation system with a data processing unit, wherein the navigation system and the data processing unit are configured and programmed in such a manner that position and/or orientation data of the referencing unit are determinable in relation to the coordinate system;
- a calibration unit, the position and/or orientation data of which are determinable in relation to the coordinate system by the navigation system, wherein the calibration unit and the at least one referencing unit can be brought into a one-to-one calibration position relative to one another, in which the calibration unit and the at least one referencing unit respectively assume a defined calibration position and/or orientation relative to one another, wherein the navigation system and the data processing unit are further configured and programmed in such a manner that position and/or orientation data of the calibration unit are determinable in relation to the coordinate system, that calibration position and/or orientation data of the referencing unit in the calibration position can be calculated on the basis of the calibration position and/or orientation data of the calibration unit, and that the calibration position and/or orientation data calculated for the at least one referencing unit in the calibration position can be assigned to the at least one referencing unit.

The surgical calibration device proposed according to the invention enables referencing units of surgical navigation systems fitted with at least one inertial sensor to be calibrated in a simple manner in relation to a spatial coordinate system. This calibration, also referred to as referencing, can be readily performed by means of the calibration unit as well as the navigation system and allows the use of referencing units fitted with inertial sensors in particular for determining the position and/or orientation of surgical devices, e.g. instruments and/or implants.

It is advantageous if the navigation system and the data processing unit are further configured and programmed in such a manner that a non-fixed coordinate system is predefinable as coordinate system, and that an origin of the non-fixed coordinate system is predefinable by the calibration position and/or orientation data of the at least one referencing unit or the calibration unit in the calibration position. It is possible with such a calibration device to also conduct a relative position and/or orientation determination of the at least one referencing unit in relation to a non-fixed coordinate system.

According to a preferred embodiment of the invention it can be provided that the navigation system and the data processing unit are further configured and programmed in such a manner that at least two referencing units can be calibrated, that a non-fixed coordinate system is predefinable as coordinate system, and that an origin of the non-fixed coordinate system is predefinable by one of the at least two referencing units. It is possible with the thus further developed navigation system to define one of the at least two referencing units as non-fixed origin of a coordinate system. In particular, it is equally possible to also use one of the at least two referencing units as calibration unit. The only condition here is that the at least two referencing units can be brought into a one-to-one calibration position relative to one another.

It is advantageous if an origin calibration gauge is provided, and if the navigation system and the data processing unit are further configured and programmed in such a manner that a spatially fixed origin of an absolute coordinate system defined by the origin calibration gauge is predefinable, if the calibration unit can be brought into an origin calibration position relative to the origin calibration gauge, in which position the calibration unit is positioned in a defined relation to the fixed origin, and if origin position and/or orientation data of the calibration unit in the origin calibration position in relation to the fixed origin can be assigned to the calibration unit. In particular, the origin calibration gauge enables the calibration unit to be brought into a one-to-one origin calibration position in relation to an origin of a spatially fixed absolute coordinate system. The calibration gauge could also be used to define the origin of the coordinate system. For example, a link between referencing units fitted with inertial sensors and referencing units fitted with conventional marker elements can also be achieved by means of the origin calibration gauge. For this, the origin calibration gauge can be fitted with conventional marker elements, for example, which allow the spatial position of the origin calibration gauge to be determined with a detection device of the navigation system.

A calibration signal generating device is advantageously provided for generation of a calibration signal when the calibration unit and the at least one referencing unit assume the calibration position. Therefore, the calibration signal generating device serves, inter alia, to generate a calibration signal if the geometric requirements for a calibration or referencing are met, i.e. when the calibration unit and the at least one referencing unit assume the calibration position.

The calibration signal generating device is favourably configured in such a manner that the calibration signal is only generated after a holding time $t_H$, during which the calibration unit and the at least one referencing unit assume the calibration position without or substantially without any relative movement. As a result of such a calibration signal generating device it can be ensured that a calibration is only performed when the calibration unit and the at least one referencing unit also actually assume the desired one-to-one calibration position.

It is advantageous if at least one actuating element is provided, which can be actuated in the calibration position, and if the calibration signal can only be generated with the calibration signal generating device during or as a consequence of an actuation of the at least one actuating element. Therefore, a condition for the generation of a calibration signal is an actuation of the at least one actuating element. In this case, the calibration signal generating device can be configured in such a manner that the calibration signal is constantly generated during an actuation of the actuating element. It can also be provided that the calibration signal is generated immediately upon actuation of the actuating element. Alternatively, it is also possible to only generate the calibration signal after the holding time, i.e. that the actuating element must be actuated at least during an uninterrupted time period corresponding to the holding time.

The at least one actuating element is preferably arranged in such a manner that it can be actuated by means of the calibration unit and/or the at least one referencing unit. Therefore, this allows in particular the actuating element to forcibly be actuated when the calibration unit and the at least one referencing unit assume the calibration position.

The structure of the calibration device becomes particularly simple if the at least one actuating element comprises a mechanical switching element, in particular a key or a foot switch. It would also be conceivable to configure the actuating element in the form of an optical switch or proximity switch of inductive or capacitive design. Provision of a hand of foot switch as actuating element allows an operator to initialise or activate a generation of the calibration signal by means of the calibration signal generating device in a desired manner.

A calibration of the at least one referencing unit or the calibration unit can be conducted in a particularly simple manner if the at least one actuating element is arranged on the at least one referencing unit, on the calibration unit and/or on the origin calibration gauge. In particular, the actuating element can be arranged in such a way that it is actuated automatically by the referencing unit, the calibration unit and/or the origin calibration gauge, when the at least one referencing unit and the calibration unit assume the calibration position and/or the calibration unit and the origin calibration gauge assume the origin calibration position.

According to a preferred embodiment of the invention it can additionally be provided that the navigation system and the data processing unit are further configured and programmed in such a manner that only after the calibration signal is present, the calibration position and/or orientation data of the calibration unit in the calibration position can be determined by means of the navigation system, the calibration position and/or orientation data of the at least one referencing unit in the calibration position can be calculated and the calibration position and/or orientation data calculated for the at least one referencing unit in the calibration position can be assigned to the at least one referencing unit. Such a calibration device can prevent a calibration from being conducted unintentionally. Therefore, a condition for a calibration with such a calibration device is always the presence of the calibration signal.

Advantageously, an origin calibration signal generating device is provided to generate an origin calibration signal when the calibration unit assumes the origin calibration position. Thus, it is possible to generate a defined signal when the calibration unit assumes the origin calibration position. For example, the origin calibration signal can be used to activate a calibration of the calibration unit in relation to the origin of the coordinate system.

It is favourable if the origin calibration signal generating device is configured in such a manner that the origin calibration signal can only be generated after a holding time $t_{H\_origin}$, during which the calibration unit assumes the origin calibration position without movement or substantially without movement. This further development prevents an origin calibration from being performed unintentionally. A reliable and accurate origin calibration can be achieved in particular because of the duration of the holding time.

It is favourable if an origin calibration actuating element is provided, which can be actuated in the origin calibration position, and if the origin calibration signal can only be generated during or as a consequence of an actuation of the origin calibration actuating element. The origin calibration actuating element that can also be part of the origin calibration signal generating device enables the latter in particular to be initialised in order to generate the origin calibration signal. Thus, the origin calibration actuating element also serves as a safety element to prevent the origin calibration signal from being generated in an undesirable manner. Moreover, it would also be conceivable to generate the origin calibration signal after conclusion of the actuation of the origin calibration actuating element.

Advantageously, the origin calibration actuating element is arranged in such a manner that it can be actuated by the calibration unit, a referencing device or the origin calibration gauge. Thus, it is possible in particular that the origin calibration actuating element is actuated automatically when the units or parts to be calibrated relative to one another assume the origin calibration position.

It would be optionally possible to configure the origin calibration actuating element in the form of an optical switch or a proximity switch. However, it is advantageous if the origin calibration actuating element comprises a key or foot switch. The key and also the foot switch can naturally also comprise optical or inductive or capacitive proximity switches. The advantage of such a configuration in particular is that actuation as a result of a mechanical contact is also possible.

According to a preferred embodiment of the invention it can be provided that the navigation system and the data processing unit are further configured and programmed in such a manner that the origin position and/or orientation data of the calibration unit in the origin calibration position in relation to the fixed origin can be assigned to the calibration unit only after the origin calibration signal is present. A faulty calibration or an incorrect calibration can be prevented with the navigation system configured in this way.

Advantageously, the navigation system and the data processing unit are further configured and programmed in such a manner that a navigation operation of the navigation system can be enabled for tracking any movements of the at least one referencing unit only when all referencing units necessary for the navigation operation have been calibrated with the calibration unit in relation to a common coordinate system. In this way the navigation system can be prevented from changing undesirably into an operating mode, in which position and/or orientation data of the at least one referencing unit are determinable, the so-called "navigation mode". Thus, the determination of false or erroneous coordinates can be prevented.

The navigation system advantageously comprises an operating time setting unit, with which a navigation operation can be restricted to a predefinable operating time $t_{operation}$. This prevents in particular excessively long operations in navigation mode, which can lead to unacceptable deviation in the determination of position and/or orientation data of the at least one referencing unit because of a drift of the inertial sensors.

It is favourable if the navigation system and the data processing unit are further configured and programmed in such a manner that the operating time $t_{operation}$, which is predefinable by means of the operating time setting unit, automatically begins to run when all referencing units have been calibrated with the calibration unit in relation to a common coordinate system. With such a calibration device an operator does not have to start the navigation mode him/herself, instead this can be started automatically if all conditions allowing a precise position and/or orientation data determination are met. It is to be noted that a referencing unit is also configured as or can serve as calibration unit.

In addition, errors in the determination of position and/or orientation data are prevented by a warning signal generating device being provided, with which after expiry of the operating time $t_{operation}$, an optical or acoustic warning signal can be emitted and/or with which the navigation operation can be automatically terminated. In this way, for example, an operator, who has been alerted by the optical and/or the acoustic warning signal, can terminate the navigation mode of the navigation system. Alternatively, the navigation operation can also be terminated automatically after expiry of the predefinable operating time to prevent operation faults.

The navigation system preferably comprises an operating time monitoring means, with which the operating time $t_{operation}$ can be monitored. This prevents the navigation mode from being conducted undesirably for longer than it should be because of the drift property of the inertial sensors.

In order to prevent or minimise errors in the position and/or orientation data determination as a result of a possible drift of the at least one inertial sensor, it is favourable if an operating time restriction device is provided to restrict the operating time $t_{operation}$ to a maximum time in a range of 1 second to 60 minutes, preferably in a range of between 10 seconds and 20 minutes.

The calibration unit advantageously comprises at least one inertial sensor. It would indeed be conceivable to also use a calibration unit in the form of a conventional so-called "pointer", i.e. a feeler or probing instrument, which is fitted with marker elements, the spatial positions of which can be detected by conventional navigation systems by means of electromagnetic radiation, by means of ultrasound or by means of video-optical methods. However, if only referencing units and also the calibration units are fitted with inertial sensors, then the structure of the navigation system is simplified overall, since it is not necessary to use two different detection methods for determination of position and orientation data of the at least one referencing unit and the calibration unit.

In order to forward or transmit measured values or other data from the calibration unit and the at least one referencing unit to the navigation system, it is favourable if the calibration unit and the at least one referencing unit respectively comprise at least one transmitting unit for transmitting measured values or changes of the position and/or orientation data of the calibration unit and the at least one referencing unit to the navigation system or to a detection device thereof.

For determination of the position and/or orientation data of the calibration unit and the at least one referencing unit, the navigation system preferably comprises an evaluation unit, which is configured in such a manner that absolute position and/or orientation data can be calculated for the calibration unit and/or the at least one referencing unit from acceleration values measured by means of the at least one inertial sensor.

For example, the evaluation unit can be part of the detection device or the data processing means or the navigation system.

According to a further preferred embodiment of the invention it can be provided that the evaluation unit is configured and/or programmed in such a manner that position and/or orientation change data of the calibration unit and the at least one referencing unit can be calculated from the measured acceleration values in relation to the coordinate system, and that absolute position and/or orientation data of the calibration unit and the at least one referencing unit can be calculated from the calculated position and/or orientation change data in relation to the coordinate system. Optionally, in the case of an only relative calibration in relation to a non-fixed coordinate system, the position and/or orientation change data can be used to compute relative position and/or orientation data in order to determine at least relative position and/or orientation data.

An inertial sensor unit comprising the at least one inertial sensor is preferably provided, which comprises at least three acceleration sensors and three rotation rate or rotation acceleration sensors, with which accelerations acting on the calibration instrument and/or the at least one referencing unit can be measured as a function of time in three mutually linearly independent directions and around three linearly independent rotational axes relative to one another. Such an inertial sensor unit enables spatial position changes of the calibration unit and/or the at least one referencing unit to be detected.

To be able to preset a unique relative position between the calibration unit and the at least one referencing unit in the calibration position, it is favourable if at least one calibration gauge is provided, which has at least one calibration receiving means to at least partially receive the calibration unit in the calibration position. In cases in which the calibration unit is formed by a referencing unit, two referencing units can then also be brought into a one-to-one calibration relative to one another, for example, by bringing them into engagement.

It is favourable if the at least one calibration gauge is arranged on the at least one referencing unit. Alternatively, it could also be arranged on the calibration unit.

The calibration unit and the at least one referencing unit are brought into a one-to-one calibration position relative to one another in a particularly simple manner if the at least one calibration receiving means comprises a recess, which corresponds to a part of the calibration unit and into which this one part of the calibration unit can be inserted in a positive arrangement.

Depending on whether a point, a direction or a point with associated direction is to be predefined by means of the calibration gauge, it is advantageous if the at least one calibration gauge is a one-, two- or three-dimensional calibration gauge for a position and/or orientation calibration of the at least one referencing unit and the calibration unit relative to one another. For example, a one-dimensional calibration gauge can be configured in the form of a bore, with which a cylindrical shaft or section of such a shaft can be brought into a defined orientation. A two-dimensional calibration gauge can be configured in the form of a groove, for example, a three-dimensional calibration gauge can be configured in the form of a non-circular blind bore or a non-circular groove with abutment on one side.

The origin calibration gauge advantageously has at least one origin calibration receiving means for at least partially receiving the calibration unit in the origin calibration position. Thus, the calibration unit can be inserted at least partially into the calibration receiving means in order to assume a one-to-one origin calibration position.

The structure of the origin calibration gauge becomes particularly simple if the at least one origin calibration receiving means has a recess, which corresponds to a part of the calibration unit and into which the one part of the calibration unit can be inserted in a positive arrangement.

The origin calibration actuating element and/or the actuating element can preferably be actuated manually. Thus, an operator can actuate the respective actuating element, for example, when the calibration unit, the referencing unit and/or the calibration gauge assume the necessary one-to-one relative position. Manually actuated can additionally mean that the respective actuating element can be actuated as a result of a contact or engagement with the calibration unit, the at least one referencing unit or the at least one calibration gauge.

A particularly simple and compact structure of the calibration device can be achieved if the origin calibration actuating element and/or the actuating element comprise a microswitch arranged on the origin calibration gauge and/or on the at least one referencing unit or on the calibration gauge.

BRIEF DESCRIPTION OF THE DRAWINGS

The following description of preferred embodiments of the invention serves as more detailed explanation in association with the drawing:

FIG. 1 is a schematic representation of a calibration device according to the invention;

FIG. 2 is a schematic representation of an origin calibration gauge with inserted calibration unit;

FIG. 3 is a plan view onto the origin calibration gauge in FIG. 2 in the direction of an origin calibration receiving means;

FIG. 10 is a perspective view of a further practical example of a calibration gauge;

FIG. 11 is a perspective view of a further calibration gauge;

FIG. 12 is a plan view onto the calibration gauge of FIG. 11;

DETAILED DESCRIPTION OF THE INVENTION

Figure 4:
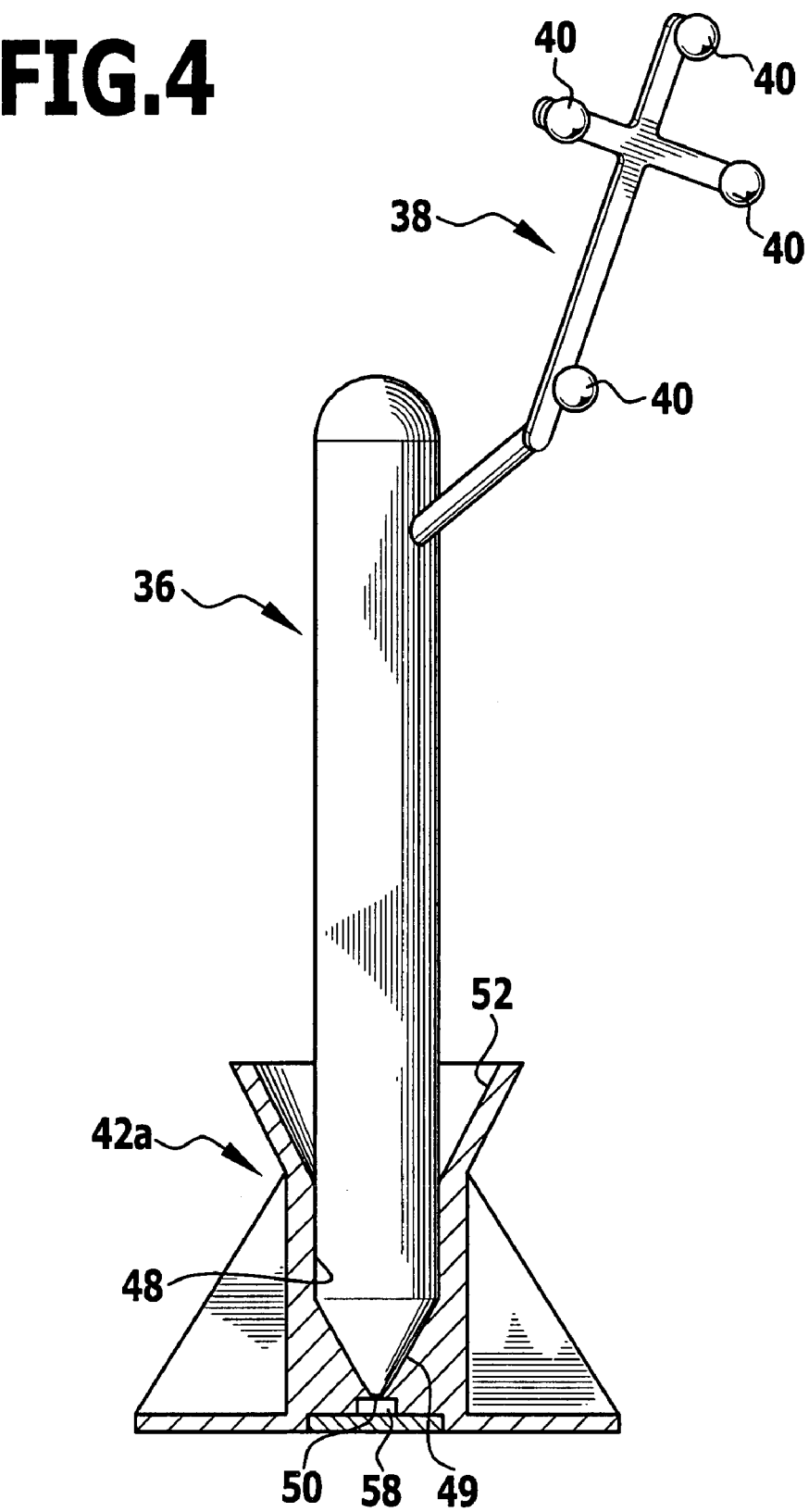
FIG. 4 shows an arrangement similar to FIG. 2 with an origin calibration gauge with an origin calibration actuating element.

An example of the application of a navigation system is shown in FIG. 1. For the determination of a centre of a knee joint of a patient 12, for example, a first referencing unit 14 is fixed on a pelvic bone 16 of the patient 12, and a second referencing unit 18 on a femur 20 of the patient 12. The fixture of the referencing units 14 and 18 on the patient 12 is generally achieved by means of bone screws or bone pins. When the femur 20 is moved relatively to the pelvic bone 16, then the referencing unit 18 describes a movement path relative to the referencing unit 14, from which a centre of rotation of the associated hip joint of the patient 12 can be determined.

A navigation system 22 serves to determine position and/or orientation of the referencing unit 14 and 18. This system comprises one or more data processing units 24, an input device 26 in the form of a keyboard as well as an output device 28 in the form of a screen, on which the input and/or output values can be displayed. The navigation system 22 further comprises a detection device 30 in order to receive data signals emitted by the referencing units 14 and 18. For this purpose, preferably three transmitting and/or receiving units 32 are used that can emit and receive electromagnetic radiation in particular in conventional systems. Other navigation systems could naturally also be used that emit and receive ultrasound in order to determine spatial positions of referencing units by means of transit-time measurements. In place of the three transmitting and/or receiving units 32, image generating devices could also be used, with which images generated using video-optical methods are evaluated and position and/or orientation data of the referencing units can be directly determined from these. In particular, such transmitting and/or receiving units 32 are also suitable for actively detecting radiation emitted by referencing units or signals reflected from these and emitted originally by the transmitting and/or receiving units 32.

The present invention relates to the calibration of a spatial position and/or orientation of at least one surgical referencing unit of a surgical navigation system fitted with at least one inertial sensor in relation to a spatial coordinate system. Therefore, at least one of the two referencing units 14 or 18 is fitted with at least one inertial sensor. Inertial sensors are used to measure forces or accelerations acting on them. Consequently, when they are moved from a first position to a second position they deliver measured values that correspond to forces and/or accelerations acting on them as a result of the change of position and/or orientation. For the determination of three-dimensional position and/or orientation changes of the referencing units 14 or 18, inertial sensor units 34 are provided that comprise at least six inertial sensors, namely three linear acceleration sensors and three rotation rate or rotation acceleration sensors arranged in such a manner that forces or accelerations are detectable in three mutually linearly independent directions. Moreover, the referencing units 14 or 18 are preferably fitted with transmitting units (not shown) to transmit force or acceleration values measured by the at least one inertial sensor to the detection device 30 of the navigation system 22, e.g. by means of Bluetooth technology.

Since an absolute position and/or orientation determination is not possible by referencing units fitted with inertial sensors, and moreover inertial sensors are subject to greater or lesser drift, depending on design, an at least single calibration or referencing of the referencing units 14 and 18 is required to predefine their position and/or orientation in relation to a coordinate system. The drift of the inertial sensors, i.e. a deviation of the actually determined measured values from the values to be theoretically expected that increases with increasing measurement duration, additionally renders it necessary to restrict an operating time $t_{operation}$ of the navigation system 22 to a time that is significantly shorter than a drift time $t_{drift}$ of the inertial sensors, which can be defined, for example, as the time that passes until a deviation of the position and/or orientation determined by means of the inertial sensors is greater than a predefined acceptable deviation, which can lie in a range of 0.10% to 50%, for example. Therefore, it is not only expedient but also even recommended because of the most accurate possible desired position and/or orientation determination of the referencing units 14 and 18 to regularly subsequently calibrate or reference the position and/or orientation thereof in the coordinate system.

A surgical calibration device according to the invention, given the overall reference 10, comprising a calibration unit 36 serves to calibrate the referencing units 14 or 18. The calibration unit can be configured in particular in the form of a feeler or probing instrument, which is also referred to or known as a "pointer". In a first variant, the calibration unit 36 is fitted with a marker element 38 shown in FIG. 1, which comprises four spheres 40 that reflect electromagnetic radiation and are fixed spatially relatively to one another in the above-defined manner. These can reflect electromagnetic radiation emitted by the detection device 30, for example, so that the spatial position of the marker element 38 is uniquely determinable by means of the navigation system 22. Moreover, the marker elements 38 can also be configured actively, i.e. active transmitting elements can be provided instead of the spheres 40. Instead of the marker element 38 shown in FIG. 1, a marker element can also be provided that is navigable by means of navigation systems that react to electromagnetic radiation, are based on ultrasound or can determine a spatial position and/or orientation of the marker element using video-optical methods. Alternatively, instead of the marker element 38 at least one inertial sensor can also be provided, preferably an inertial sensor unit with six inertial sensors, namely three linear acceleration and three rotation acceleration sensors, which are arranged and configured in such a manner that they can detect accelerations and/or forces acting on the calibration unit in three mutually linearly independent directions. As an option, it would also be conceivable to also provide the marker element 38 in addition to the inertial sensor unit (not shown). In the case of a calibration unit fitted with at least one inertial sensor a transmitting unit is also preferably provided, with which the measured values detected by the at least one inertial sensor can be transmitted to the navigation system 22. A cable-connected calibration unit, i.e. a calibration unit connected to the navigation system by means of a cable, can naturally also be provided, which has the advantage that no interfering external influences can impair a data transfer between the calibration unit and the navigation system. In particular, a data exchange can be performed using Bluetooth technology.

A calibration of the referencing units 14 and 18 can be performed, for example, in a fixed spatial coordinate system 60, e.g. an operating theatre. In particular, an origin can be defined by means of an origin calibration gauge 42. This is a spatially fixed device arranged, for example, on a table top 44 or an operating table 46, which can have a receiving means 48, into which a part of the calibration unit 36 can be inserted, i.e. preferably in a positive and one-to-one arrangement. In this case, one-to-one means that there is precisely only one possibility of inserting the calibration unit 36 into the receiving means 48.

The origin calibration gauge 42 shown by way of example in FIG. 2 comprises a receiving means 48 with a hexagonal cross-section, which tapers in a cone shape at its closed end. A distal end 49 of the calibration unit 36 with a probe tip 50 is configured to correspond to the receiving means 48, i.e. the distal end 49 widens in a cone shape from the probe tip 50 and is extended by a section 51 with a hexagonal cross-section. To enable the distal end 49 of the calibration unit 36 to be inserted more easily into the receiving means 48, this widens into a funnel shape pointing away from its closed end, so that a inside face 52 of this cone envelope-shaped section forms a surface for the distal end 49 of the calibration unit 36 to slide onto.

The origin calibration gauge 42, which optionally can also be fastened to a circumferentially arranged rail on the operating table in the operating theatre or on an instrument table, thus defines a so-called absolute or global coordinate system 60. It is naturally also conceivable to provide the origin calibration gauge 42 with a different internal cross-section, so that a distal end of the calibration unit 36, which is then shaped accordingly, can be inserted into the receiving means 48 only on a one-to-one orientation in accordance with the lock and key principle.

To assign the fixed coordinate system 60 defined by the origin calibration gauge 42 to the calibration unit 36, i.e. to perform an absolute referencing or calibration, the distal end 49 of the calibration unit 36 is inserted into the receiving means 48 of the origin calibration gauge 42. In one possible construction, a switch 56 can be arranged on the elongated cylindrical body 54 of the calibration unit 36. If the switch 56 is actuated, e.g. by an operator, as a result of a corresponding configuration of the navigation system 22, this results in the calibration unit 36 being calibrated, which is also referred to as "zeroing". In particular, the coordinates of the origin of the fixed coordinate system 60 can be assigned to the calibration unit 36 when the probe tip 50 is zeroed. If the origin calibration unit 42 does not define the origin of the fixed coordinate system 60, then alternatively the spatial position and/or orientation thereof can also be assigned to the probe tip 50 of the calibration unit 36, if these data are known. Optionally, the coordinates can be determined by means of the navigation system 22 if a marker element similar to marker element 38 is arranged on the origin calibration gauge. A spatial position of the origin calibration gauge 42 can then be determined, for example, with reference to the detection device 30.

An alternative procedure for the zeroing of the calibration unit 36 is that this so-called zeroing is performed when the position and/or orientation of the calibration unit 36, which are monitored by the navigation system 22, do not or hardly change for a specific holding time $t_{hold}$, e.g. for at least 3 to 30 seconds, preferably 5 to 7 seconds. The assignment of position and/or orientation data to the calibration unit 36 assuming an origin calibration position can then occur automatically.

A further variant lies in providing a foot switch as actuating element for an operator in place of actuation of the switch 56. The navigation system 22 or the data processing unit 24 can be configured and/or programmed in such a manner that a calibration signal that initialises the "zeroing" is generated as a result of the actuation of the foot switch or also of switch 56.

In a further variant of an origin calibration, an alternative origin calibration gauge 42a is used. This has substantially the same structure as the origin calibration gauge 42, but at the closed end of the receiving means 48 a microswitch 58 is arranged, which is actuated by the probe tip 50 of the calibration unit 36 when a distal end 49 thereof penetrates into the receiving means 48 in a defined manner and assumes the origin calibration position. The zeroing of the calibration unit 36 can be initialised by actuating the microswitch 58. An actuating element is not absolutely necessary on the calibration unit to activate the origin calibration process when using the origin calibration gauge 42a.

If the calibration unit 36 fitted with at least one inertial sensor is calibrated in the origin coordinate system, then this can be used in a following step for referencing the referencing units 14 and/or 18 in this coordinate system 60. For this, the tip 50 of the calibration unit 36 can be moved close to the referencing units 14 and 16, for example, or can be at least partially inserted into a receiving means 62 corresponding to the distal end 49 of the calibration unit 36. In this way, a unique calibration position is predefined, for example, between the calibration unit 36 and the referencing units 14 or 18 at least for a point and/or a direction. The receiving means 62 can also be part of a calibration gauge, which is arranged on the referencing unit 14 or 18. Conversely, such a calibration gauge can also be provided on the calibration unit 36, so that a part of the referencing units 14 or 18 can also be inserted, for example, into a receiving means (not shown in the figures) provided for this on the calibration unit 36.

The referencing or calibration of the referencing units 14 and 18 can be initialised in particular by a microswitch, which is arranged, for example, on each of the referencing units 14 or 18 and is actuated in the calibration position by the probe tip 50 of the calibration unit 36, for example. Alternatively, as in the case of the origin calibration, a referencing of the referencing units 14 or 18 can occur if a relative position between the calibration unit 36 and the referencing units 14 or 18 does not change for a specific predefinable holding time $t_{hold}$. The holding time $t_{hold}$ can be predefined in a time window of 3 seconds to 30 seconds, for example. Therefore, when the calibration unit 36 and the referencing unit 14 or 18 to be referenced assume the calibration position for a specific time, then the known position and/or orientation data of the calibration unit 36 can be assigned to the respective referencing unit 14 or 18 by the navigation system 22. The position and/or orientation of the referencing unit 14 or 18 are then known in the fixed coordinate system 60.

In order to prevent faults in a measurement of spatial movements or movement paths of the referencing units 14 and 18, the navigation system 22 can be configured in particular in such a manner that a detection of the movement paths of the referencing units 14 and 18, i.e. a so-called navigation operation, can only be activated when the positions of the referencing units 14 and 18 or possibly further referencing units have been referenced in the coordinate system 60. The activation for the navigation operation is performed automatically by the navigation system 22 in particular. Moreover, the navigation system 22 is configured and, if necessary, programmed in such a manner that the navigation operation is or can be temporally restricted to an operating time $t_{operation}$. Because of the drift of the inertial sensors, the navigation operation can be restricted to an operating time $t_{operation}$ in a range of 1 second to 60 minutes. The operating time $t_{operation}$ is preferably restricted to 5 minutes. The operating time $t_{operation}$ can be monitored in particular by an operating time monitoring device, which can be part of the navigation system 22 or its data processing unit 24. After expiry of the operating time $t_{operation}$, an acoustic and/or optical warning signal can sound, so that an operator of the navigation system 22 is alerted to the end of the navigation operation.

Optionally, the navigation operation can also be terminated automatically by the navigation system 22.

After expiry of the operating time $t_{operation}$, a renewed referencing of the referencing units 14 and 18 fitted with inertial sensors and possibly also of the calibration unit 36 is required. As described above, for this, the calibration unit 36 is firstly referenced by means of the origin calibration gauge 42 and then the operation proceeds as further described.

Figure 5:
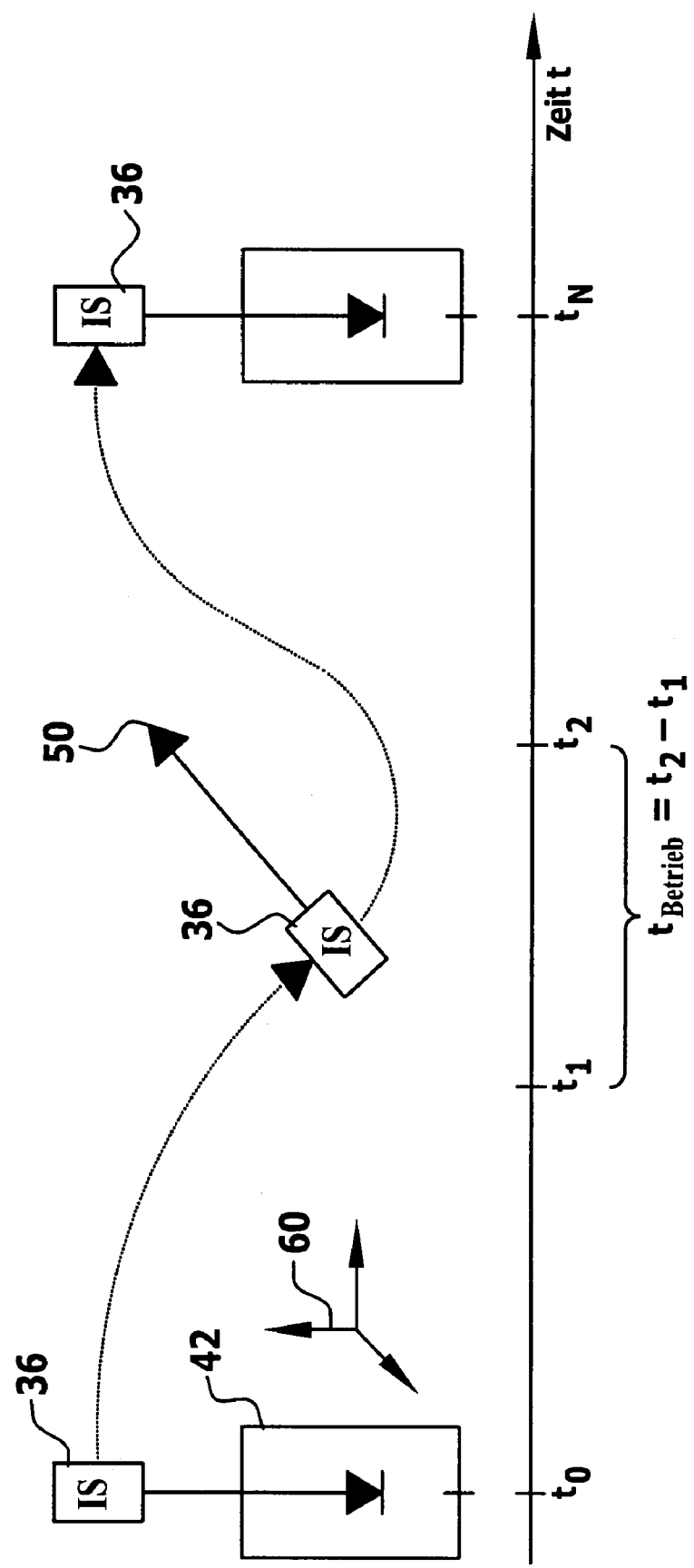
FIG. 5 is a schematic representation of a calibration of a referencing unit in a fixed coordinate system.

The origin calibration of the calibration unit 36 is shown schematically in FIG. 5. At time point $t_0$, the calibration unit 36 is calibrated by means of the origin calibration gauge 42 in the fixed coordinate system 60. One referencing unit after the other can then be referenced in the fixed coordinate system 60 by means of the calibration unit 36. The operating time $t_{operation}$ of the navigation operation begins, for example, at time point $t_1$, at which all referencing units 14 and 18 have been referenced. After expiry of the operating time $t_{operation}$, i.e. at time point $t_2$, the measurement inaccuracies become so great as a result of a drifting of the inertial sensors that no further meaningful, i.e. sufficiently precise, navigation operation can be conducted. The calibration unit 36 must therefore be calibrated again, e.g. at time point $t_N$.

In cases where a referencing is not necessary in a fixed coordinate system, the above-described step of referencing of the calibration unit 36 can be omitted. Instead of this, it is sufficient to bring the calibration unit 36 and the referencing units 14 or 18 respectively into a calibration position. For this, calibration gauges 64 or 66 can optionally be arranged on the referencing units 14 and 18, which assure a geometrically one-to-one relative position between the calibration unit and the referencing units 14 or 18. For example, in a similar manner to the origin calibration gauge 42, the calibration gauges 64 and 66 can have receiving means 62, into which a distal end of the calibration unit 36 can be inserted with the probe tip 50 first.

A so-called relative referencing can then be conducted in the following manner. When the calibration unit 36 and the referencing unit 14 assume the calibration position in a defined manner, a calibration signal can be generated in particular. This can be initialised by an operator, e.g. by actuation of a hand or foot switch. The calibration signal can also be generated automatically, if the calibration position is assumed for a specific time $t_{hold}$. Alternatively, an actuating element can also be actuated automatically and generate a calibration signal, when the calibration unit 36 and the referencing unit 14 assume the calibration position. For example, the referencing unit 14 can be fitted with a microswitch, which, in a similar manner to the microswitch 58, can be actuated by the probe tip 50. The microswitch could naturally also be arranged on the calibration unit 36 and actuated by an associated projection on the referencing unit 14 in the calibration position. The inertial sensors of the referencing unit 14 and the calibration unit 36 determine forces acting on both units. As a result of the calibration, the force measured values at time point $t_0$ of the calibration can be set to 0 for both inertial sensors. Thus, an origin of a non-fixed coordinate system is virtually defined at time point $t_0$. All measurements of location and/or orientation of the referencing unit 14 and the calibration unit 36 can be subsequently determined in relation to the calibration position. In particular, further referencing units, e.g. referencing unit 18, can be referenced relative to the calibration position of the calibration unit 36 and the referencing unit 14, i.e. by bringing the calibration unit 36 into a calibration position relative to the referencing unit 18 and then assigning the position and/or orientation of the calibration unit 36 to this in relation to the non-fixed coordinate system. When all referencing units have been referenced in the described manner, the operating time $t_{operation}$, during which a navigation operation is possible, i.e. the referencing units 14 and 18 can be moved as desired and their movement paths detected by the navigation system 22, runs as already described above. Moreover, during the navigation operation with the calibration unit 36 any desired spatial points can also be probed, i.e. depending on whether an absolute or relative referencing has been performed in relation to a fixed or non-fixed coordinate system.

Figure 7:
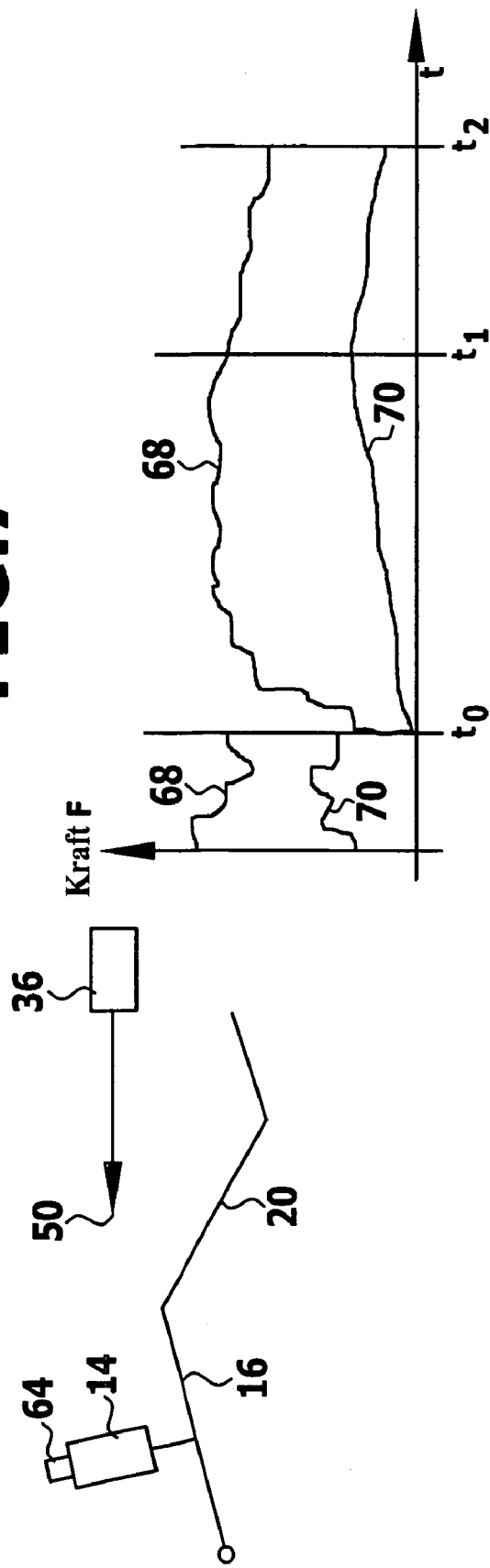
FIG. 7 is a schematic representation of a calibration method similar to the method sketched in FIG. 6.

The procedure with the relative referencing in a non-fixed coordinate system is shown schematically in FIG. 7, wherein the forces 68 acting on the inertial sensors and the referencing units 14 are shown by way of example and as a function of time in the graph.

In a further variant of the method according to the invention a relative referencing of the referencing units 14 and 18 can also be performed as follows. At time point $t_0$ both referencing units 14 and 18 are "zeroed" by the navigation system 22, i.e. at time point $t_0$ the signals generated by the inertial sensors of the referencing units 14 or 18 are set to zero. To enable relative movements of the two referencing units 14 and 18 to be determined relative to one another in a desired manner, the two referencing units 14 and 18 are probed one after the other with the calibration unit 36, or in other words the calibration unit 36 is respectively brought into a calibration position with referencing unit 14 and with referencing unit 18 in succession. If in the first calibration position, e.g. in the calibration position of the calibration unit 36 relative to the referencing unit 14, position and/or orientation of the referencing unit 14 are assigned to the calibration unit 36, then a spacing between the two referencing units 14 and 18 can be determined in a simple manner by next moving the calibration unit 36 into a calibration position relative to the referencing unit 18. Any desired position and/or orientation changes of the referencing units 14 and 18 can then be detected and output by means of the navigation system 22. After expiry of the operating time $t_{operation}$, the referencing unit 14 and 18 can be automatically zeroed again, for example. This means that a measured value of 0, for example, is assigned again to the referencing unit 14 and a measured value corresponding to the difference at the end of the operating time $t_{operation}$ is assigned to referencing unit 18. As a result of this, the relative positions of the referencing units 14 and 18 to one another are maintained and it is then not necessary to determine the spacing once again by means of the calibration unit 36.

Figure 6:
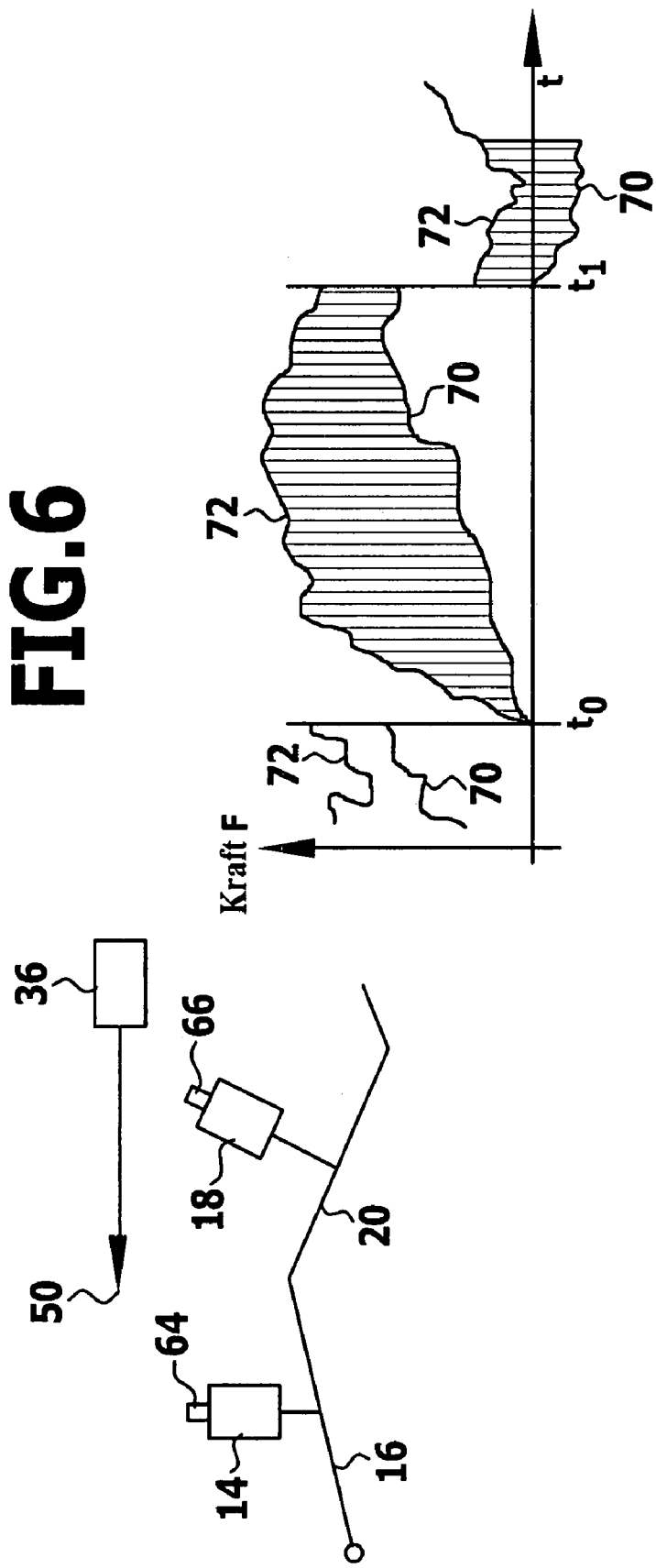
FIG. 6 is a schematic representation of a relative calibration of referencing units in a non-fixed coordinate system.

The procedure in the relative referencing in the last-mentioned case is shown schematically in FIG. 6, wherein the time-dependent force curves 70 and 72 correspond to the forces acting on the inertial sensors of the referencing units 14 or 18 in an exemplary manner.

An appropriate referencing is necessary, depending on whether positions and/or orientations in the coordinate system are to be determined with the referencing units 14 or 18. For this the referencing units 14 and 18 can be fitted, for example, with so-called calibration gauges, which are matched geometrically to a part or section of the calibration unit 36 in order to define a unique orientation, a unique position or a unique position including orientation. This also applies analogously to the above-described origin calibration, and therefore the calibration gauges described below could also serve, in principle, as origin calibration gauges. It should also be noted that the calibration gauges, as described below by way of example, can also be arranged on the calibration unit 36 and brought into engagement with corresponding sections or parts of the referencing units 14 or 18.

Figure 8:
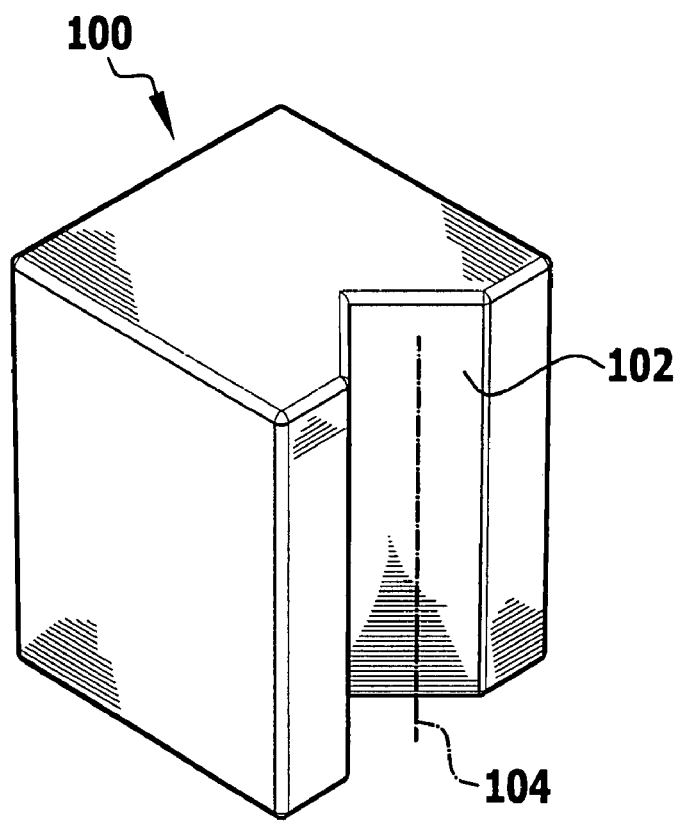
FIG. 8 is a perspective view of a calibration gauge.
Figure 9:
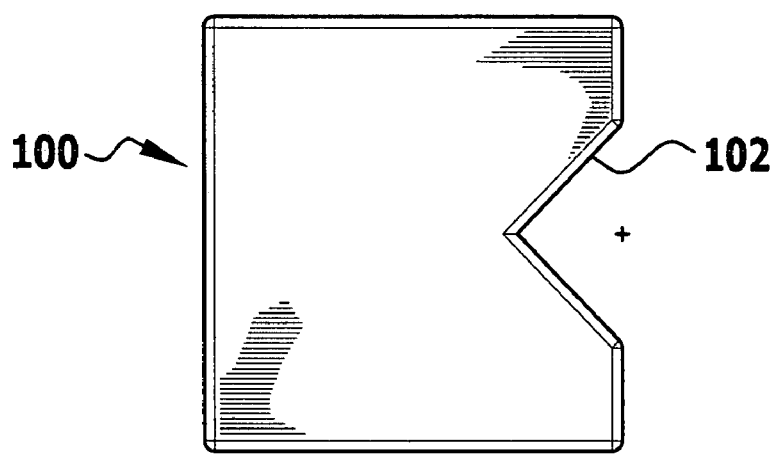
FIG. 9 is a plan view onto the calibration gauge of FIG. 8.

To predefine an axis, a calibration gauge 100 can be used, for example, which is substantially cuboidal in shape and has a wedge-shaped groove 102 extending parallel to the side edges. A cylindrical section of the calibration unit can be placed against the groove 102 and thus define an axis 104. The calibration gauge 100 is shown schematically in FIGS. 8 and 9.

An alternative calibration gauge 110 for defining an axis 112 is shown in FIG. 10. The axis 112 is defined by a passage 114 through the substantially cuboidal body of the calibration gauge 110. The calibration gauge 110 can optionally also be provided with a cuboidal projection 116, which protrudes from a side face 118 and likewise defines an axis. However, the projection 116 can also serve as a universal adapter to connect the calibration gauge 110 to one of the referencing units 14 or 18 or the calibration unit 36.

The calibration gauge 120 shown schematically in FIGS. 11 and 12 enables both an axis 122 and a spatial point to be predefined. For this purpose, a substantially cuboidal base body of the calibration gauge 120 is provided with a blind hole 124, the base 126 of which defines an abutment, e.g. for the probe tip 50 of the calibration unit 36.

Figure 13:
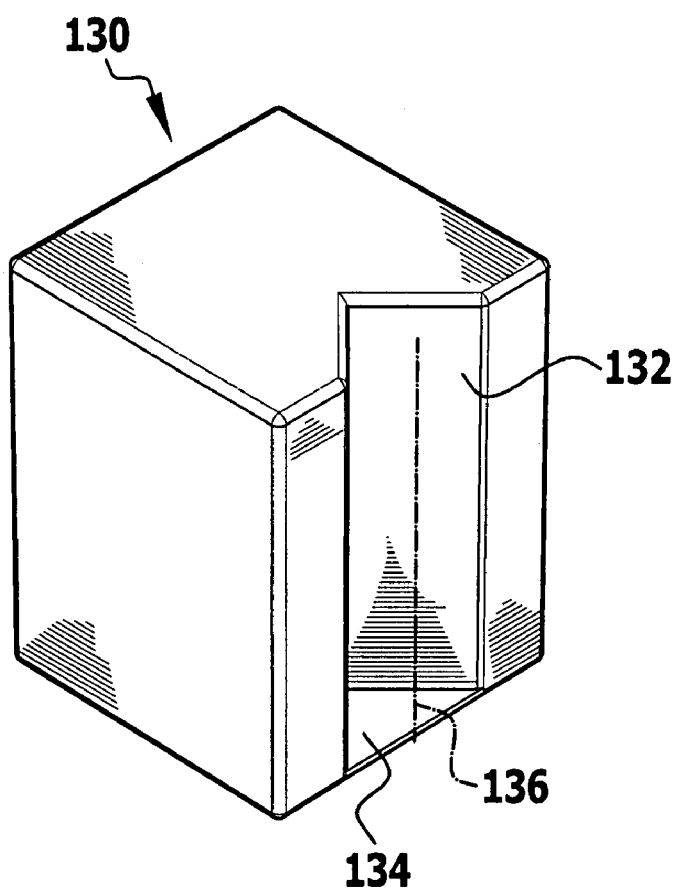
FIG. 13 is a perspective view of a further practical example of a calibration gauge for point-direction calibration.
Figure 14:
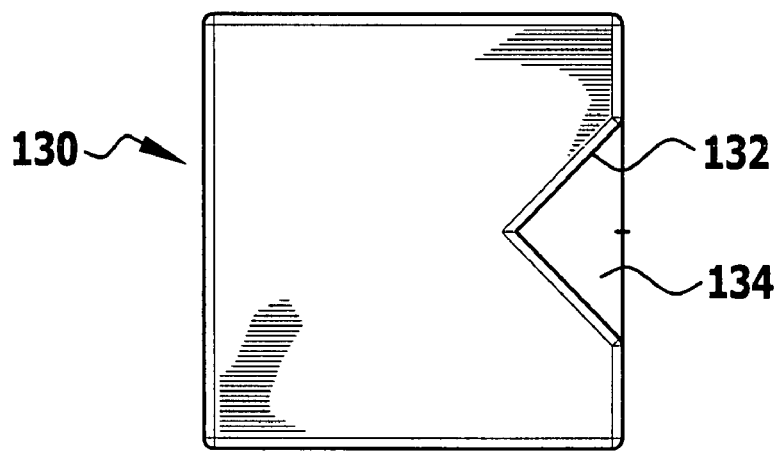
FIG. 14 is a plan view onto the calibration gauge of FIG. 13.
Figure 15:
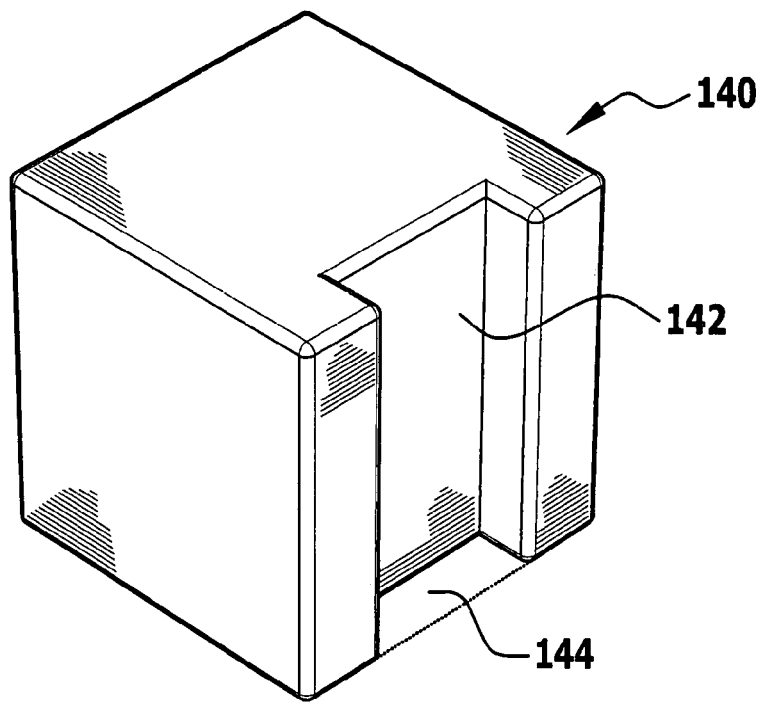
FIG. 15 is a perspective view of a "two-" or "three-dimensional" calibration gauge.
Figure 16:
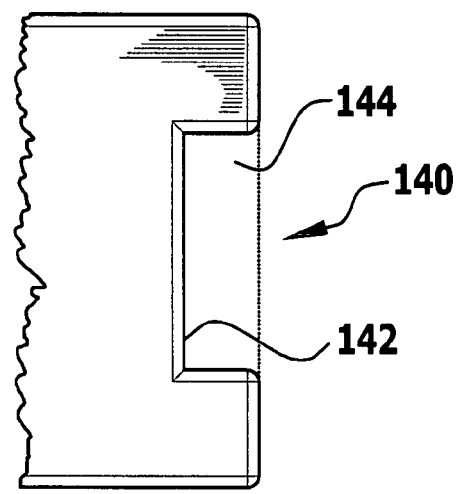
FIG. 16 is a plan view onto a section from the calibration gauge of FIG. 15.
Figure 17:
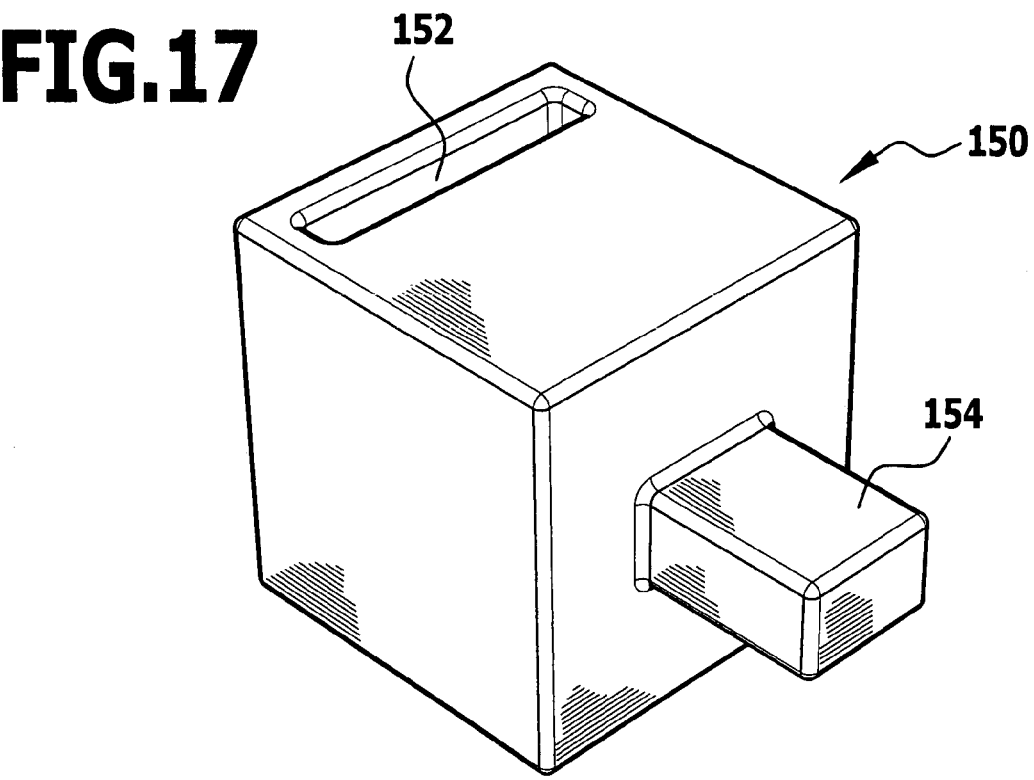
FIG. 17 is a perspective view of a further practical example of a "two-" or "three-dimensional" calibration gauge.
Figure 18:
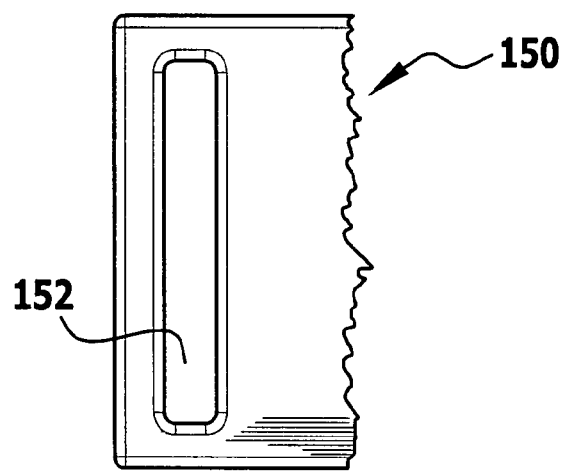
FIG. 18 is a plan view on to a part of the calibration gauge shown in FIG. 17.

Similarly, a point and an axis for an instrument navigation can be performed with the calibration gauge 130 shown in FIGS. 13 and 14, which substantially corresponds to the calibration gauge 100, i.e. likewise has a wedge-shaped groove 132 in a side face parallel to side edges of the cuboidal body of the calibration gauge 130. In addition, an abutment 134 is provided, through which the axis 136 defined by the groove 132 passes. The abutment 134 serves, for example, as abutment for the probe tip 50 of the calibration unit 36 for definition of a point.

For referencing planes in a coordinate system, the calibration gauges 140 and 150 shown schematically in FIGS. 15 and 16 or 17 and 18 are used. They can additionally be used as sawing gauges. The calibration gauge 140 comprises a substantially cuboidal body, which has a shallow cuboidal groove 142 in one side face that can optionally be closed off at one end with an abutment 144. For example, a saw blade can be inserted into the groove 142 and guided in this. When the calibration gauge 140 is brought into a desired position in a fixed or non-fixed coordinate system in a desired manner, the calibration gauge 140 can also be used directly as sawing gauge to perform a cut on the tibia or femur of a patient, for example.

For definition of a plane, the calibration gauge 150 is provided with a slot 152, which can be configured in particular as a through slot or as a slot in the form of a blind hole. The slot 152 can in particular also serve as a guide for a saw blade. A cuboidal projection optionally protruding from a side face of the calibration gauge 150 can serve as an adapter 154 for connecting the calibration gauge 150 to one of the referencing units 14 or 18 or the calibration unit 36.

Figure 19:
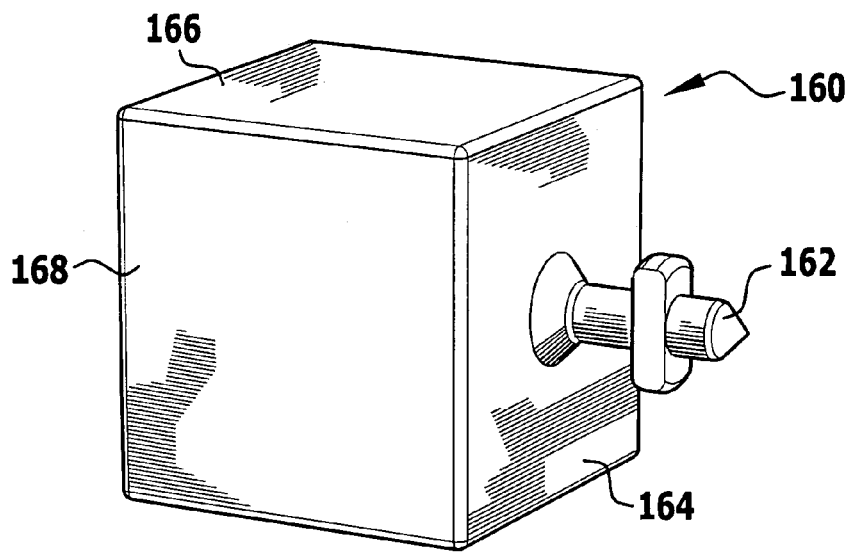
FIG. 19 is a perspective view of a further "three-dimensional" calibration gauge.

The calibration gauge 160 shown schematically in FIG. 19 substantially comprises a cuboidal base body with an adapter 162, which protrudes perpendicularly from a side face 164 and which is not rotationally symmetric in order to define security against rotation upon connection of the calibration gauge 160 to one of the referencing units 14 or 18 or the calibration unit 36. Further side faces 166 and 168 of the calibration unit 160 are used for defining planes, e.g. for saw cuts to be performed. In addition, the side faces 166 and 168 can also be provided with lateral boundary abutments for additional guidance of a saw blade.

Figure 20:
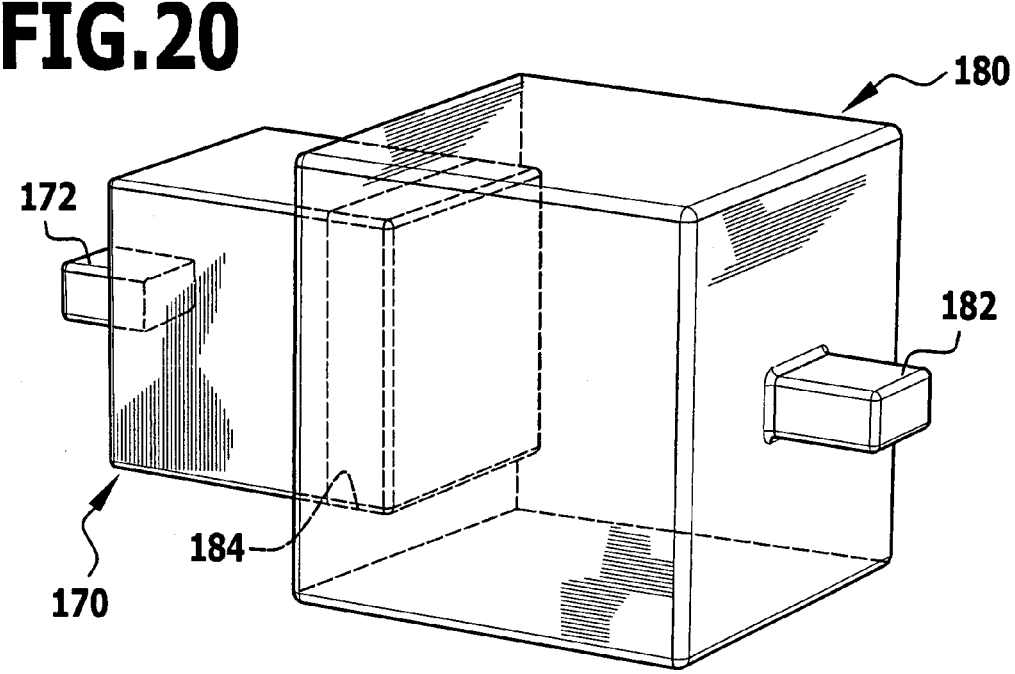
FIG. 20 is a perspective view of two calibration gauges engaged in a calibration position.

An example of two calibration gauges 170 and 180 that can be brought together into a one-to-one calibration position is shown in FIG. 20. The calibration gauge 180 has a cuboidal receiving means 184 for this, into which a part of the calibration gauge 170 can be inserted in a positive arrangement. Both calibration gauge 170 and calibration gauge 180 are respectively provided with a cuboidal projection that extends perpendicularly from a respective side face and forms an adapter 172 or 182 for connection to a referencing unit 14 or 18 or the calibration unit 36. It would naturally also be conceivable to use one of the two calibration gauges 170 or 180 as origin calibration gauge.

The calibration gauges shown in FIGS. 8 to 20 are only meant as examples to perform one-dimensional referencing, i.e. direction referencing, two-dimensional referencing, e.g. plane referencing, and three-dimensional referencing, in particular point-direction referencing. Naturally, the precise dimensions of the calibration gauges and their fittings can be previously determined prior to use in association with a navigation system 22 for a high-precision navigation operation. Thus, for example, a relative position between the probe tip 50 and the calibration gauge arranged on the calibration unit 36 can be determined with high precision. In this way, a position and/or orientation of the probe tip 50 can always be determined with high precision from a position and/or orientation of the calibration gauge determined by means of the navigation system 22.

What is claimed is:

1. Method for calibrating a spatial position and/or orientation of at least one surgical referencing unit of a surgical navigation system fitted with at least one inertial sensor in relation to a spatial coordinate system, comprising:
   providing a calibration unit, the position and/or orientation data of which are determinable in relation to the spatial coordinate system by the navigation system;
   bringing the calibration unit and the at least one referencing unit into a one-to-one defined position relative to one another;
   determining in the spatial coordinate system first calibration position and/or orientation data of the calibration unit in the defined position by means of the navigation system;

calculating in the spatial coordinate system second calibration position and/or orientation data of the referencing unit in the defined position on the basis of the first calibration position and/or orientation data of the calibration unit, and assigning the second calibration position and/or orientation data calculated for the at least one referencing unit in the defined position to the at least one referencing unit as initial position and/or orientation data of the referencing unit in the spatial coordinate system.

2. Method according to claim 1, wherein:
the spatial coordinate system comprises a non-fixed coordinate system, and
an origin of the non-fixed coordinate system is predefined by one of the first calibration position and/or orientation data of the calibration unit or the second calibration position and/or orientation data of the at least one referencing unit.

3. Method according to claim 1, wherein:
at least two referencing units are calibrated,
the spatial coordinate system comprises a non-fixed coordinate system, and
an origin of the non-fixed coordinate system is predefined by one of the at least two referencing units.

4. Method according to claim 1, wherein:
the spatial coordinate system comprises an absolute coordinate system;
a spatially fixed origin of the absolute coordinate system is predefined,
the calibration unit is initially brought into an origin calibration position, in which the calibration unit is positioned in a defined relation to the fixed origin, and
origin position and/or orientation data of the calibration unit in the origin calibration position relative to the fixed origin are assigned to the calibration unit.

5. Method according to claim 1, wherein a calibration signal is generated when the calibration unit and the at least one referencing unit assume the defined position.

6. Method according to claim 5, wherein the calibration signal is only generated after a holding time $t_H$, during which the calibration unit and the at least one referencing unit assume the defined position without or substantially without any relative movement.

7. Method according to claim 5, wherein:
an actuating element is actuated in the defined position, and
the calibration signal is only generated during or as a consequence of an actuation of the actuating element.

8. Method according to claim 7, wherein the actuating element is actuated by means of the calibration unit and/or the at least one referencing unit.

9. Method according to claim 7, wherein a key or a foot switch is used as actuating element.

10. Method according to claim 5, wherein:
only after the calibration signal is present is the first calibration position and/or orientation data of the calibration unit in the defined position determined by means of the navigation system.

11. Method according to claim 4, wherein an origin calibration signal is generated when the calibration unit assumes the origin calibration position.

12. Method according to claim 11, wherein the origin calibration signal is only generated after a holding time $t_{H\_origin}$, during which the calibration unit assumes the origin calibration position without movement or substantially without movement.

13. Method according to claim 11, wherein:
in the origin calibration position an origin calibration actuating element is actuated, and
the origin calibration signal is only generated during or as a consequence of an actuation of the origin calibration actuating element.

14. Method according to claim 13, wherein the origin calibration actuating element is actuated by the calibration unit or a referencing device.

15. Method according to claim 13, wherein a key or foot switch is used as origin calibration actuating element.

16. Method according to claim 11, wherein the origin position and/or orientation data of the calibration unit in the origin calibration position in relation to the fixed origin are assigned to the calibration unit only after the origin calibration signal is present.

17. Method according to claim 1, wherein a navigation operation of the navigation system is enabled for tracking any movements of the at least one referencing unit only when all referencing units necessary for the navigation operation have been calibrated with the calibration unit in relation to a common coordinate system.

18. Method according to claim 17, wherein the navigation operation is restricted to a predefinable operating time $t_{operation}$.

19. Method according to claim 18, wherein the operating time $t_{operation}$ automatically begins to run when all referencing units have been calibrated with the calibration unit in relation to a common coordinate system.

20. Method according to claim 18, wherein after expiry of the operating time $t_{operation}$, an optical and/or acoustic warning signal is emitted and/or the navigation operation is automatically terminated.

21. Method according to claim 18, wherein the operating time $t_{operation}$ is monitored by the navigation system.

22. Method according to claim 18, wherein the operating time $t_{operation}$ is restricted to a maximum time in the range of 1 second to 60 minutes.

23. Method according to claim 1, wherein the calibration unit is fitted with at least one inertial sensor, the position and/or orientation data of which are determinable in relation to the coordinate system by the navigation system.

24. Method according to claim 1, wherein:
the calibration unit and the at least one referencing unit respectively have at least one transmitting unit, and
with the at least one transmitting units changes of the position and/or orientation data of the calibration unit and/or the at least one referencing unit during a navigation operation are transmitted to the navigation system or to a detection device thereof.

25. Method according to claim 1, wherein the navigation system comprises an evaluation unit configured in such a manner that absolute position and/or orientation data can be calculated for the calibration unit and the at least one referencing unit from acceleration values measured by means of the at least one inertial sensor during a navigation operation.

26. Method according to claim 24, wherein:
position and/or orientation change data of the calibration unit and the at least one referencing unit are calculated from the measured acceleration values in relation to the coordinate system, and
absolute position and/or orientation data of the calibration unit and the at least one referencing unit are calculated from the calculated position and/or orientation change data in relation to the coordinate system.

27. Method according to claim 1, wherein:
an inertial sensor unit is provided comprising the at least one inertial sensor,
the inertial sensor unit comprises at least three linear and three rotation acceleration sensors, with which accelerations and/or forces (F) acting on the calibration unit and/or the at least one referencing unit are measured as a function of time in three mutually linearly independent directions and around three mutually linearly independent rotational axes.

28. Surgical calibration device for calibrating a spatial position and/or orientation of at least one surgical referencing unit of a surgical navigation system fitted with at least one inertial sensor in relation to a spatial coordinate system, comprising:
a navigation system with a data processing unit, wherein the navigation system and the data processing unit are configured and programmed in such a manner that position and/or orientation data of the referencing unit are determinable in relation to the spatial coordinate system;
a calibration unit, the position and/or orientation data of which are determinable in relation to the spatial coordinate system by the navigation system, wherein:
the calibration unit and the at least one referencing unit can be brought into a one-to-one defined position relative to one another,
the navigation system and the data processing unit are further configured and programmed in such a manner that first calibration position and/or orientation data of the calibration unit are determinable in relation to the spatial coordinate system in the defined position,
second calibration position and/or orientation data of the referencing unit in the defined position can be calculated in the spatial coordinate system on the basis of the first calibration position and/or orientation data of the calibration unit, and
the second calibration position and/or orientation data calculated for the at least one referencing unit in the defined position can be assigned to the at least one referencing unit as initial position and/or orientation data of the referencing unit in the spatial coordinate system.

29. Surgical calibration device according to claim 28, wherein:
the navigation system and the data processing unit are further configured and programmed in such a manner that the spatial coordinate system comprises a non-fixed coordinate system, and
an origin of the non-fixed coordinate system is predefinable by one of the first calibration position and/or orientation data of the calibration unit or the second calibration position and/or orientation data of the at least one referencing unit.

30. Surgical calibration device according to claim 28, wherein:
the navigation system and the data processing unit are further configured and programmed in such a manner that at least two referencing units can be calibrated,
the spatial coordinate system comprises a non-fixed coordinate system, and
an origin of the non-fixed coordinate system is predefinable by one of the at least two referencing units.

31. Surgical calibration device according to claim 28, wherein:
an origin calibration gauge is provided,
the spatial coordinate system comprises an absolute coordinate system,
the navigation system and the data processing unit are further configured and programmed in such a manner that a spatially fixed origin of absolute coordinate system defined by the origin calibration gauge is predefinable,
the calibration unit is initially brought into an origin calibration position relative to the origin calibration gauge, in which position the calibration unit is positioned in a defined relation to the fixed origin, and
origin position and/or orientation data of the calibration unit in the origin calibration position in relation to the fixed origin can be assigned to the calibration unit.

32. Surgical calibration device according to claim 28, wherein a calibration signal generating device is provided for generation of a calibration signal when the calibration unit and the at least one referencing unit assume the defined position.

33. Surgical calibration device according to claim 32, wherein the calibration signal generating device is configured in such a manner that the calibration signal is only generated after a holding time $t_H$, during which the calibration unit and the at least one referencing unit assume the defined position without or substantially without any relative movement.

34. Surgical calibration device according to claim 32, wherein:
at least one actuating element is provided, which can be actuated in the defined position, and
the calibration signal can only be generated with the calibration signal generating device during or as a consequence of an actuation of the at least one actuating element.

35. Surgical calibration device according to claim 34, wherein the at least one actuating element is arranged in such a manner that it can be actuated by means of the calibration unit and/or the at least one referencing unit.

36. Surgical calibration device according to claim 34, wherein the at least one actuating element comprises a key or a foot switch.

37. Surgical calibration device according to claim 34, wherein the at least one actuating element is arranged on the at least one referencing unit, on the calibration unit and/or on an origin calibration gauge.

38. Surgical calibration device according to claims 32, wherein:
the navigation system and the data processing unit are further configured and programmed in such a manner that only after the calibration signal is present is the first calibration position and/or orientation data of the calibration unit in the defined position determined by means of the navigation system.

39. Surgical calibration device according to claim 31, wherein an origin calibration signal generating device is provided to generate an origin calibration signal when the calibration unit assumes the origin calibration position.

40. Surgical calibration device according to claim 39, wherein the origin calibration signal generating device is configured in such a manner that the origin calibration signal can only be generated after a holding time $t_{H\ origin}$, during which the calibration unit assumes the origin calibration position without movement or substantially without movement.

41. Surgical calibration device according to claim 39, wherein:
an origin calibration actuating element is provided, which can be actuated in the origin calibration position, and
the origin calibration signal can only be generated during or as a consequence of an actuation of the origin calibration actuating element.

42. Surgical calibration device according to claim 41, wherein the origin calibration actuating element is arranged in such a manner that it can be actuated by the calibration unit, a referencing device or the origin calibration gauge.

43. Surgical calibration device according to claim 41, wherein the origin calibration actuating element comprises a key or foot switch.

44. Surgical calibration device according to claim 39, wherein the navigation system and the data processing unit are further configured and programmed in such a manner that the origin position and/or orientation data of the calibration unit in the origin calibration position in relation to the fixed origin can be assigned to the calibration unit only after the origin calibration signal is present.

45. Surgical calibration device according to claim 28, wherein the navigation system and the data processing unit are further configured and programmed in such a manner that a navigation operation of the navigation system can be enabled for tracking any movements of the at least one referencing unit only when all referencing units necessary for the navigation operation have been calibrated with the calibration unit in relation to a common coordinate system.

46. Surgical calibration device according to claim 45, wherein the navigation system comprises an operating time setting unit, with which the navigation operation can be restricted to a predefinable operating time $t_{operation}$.

47. Surgical calibration device according to claim 46, wherein the navigation system and the data processing unit are further configured and programmed in such a manner that the operating time $t_{operation}$, which is predefinable by means of the operating time setting unit, automatically begins to run when all referencing units have been calibrated with the calibration unit in relation to a common coordinate system.

48. Surgical calibration device according to claim 46, wherein a warning signal generating device is provided, with which after expiry of the operating time t,operation, an optical and/or acoustic warning signal can be emitted and/or with which the navigation operation can be automatically terminated.

49. Surgical calibration device according to claim 46, wherein the navigation system comprises an operating time monitoring means, with which the operating time $t_{operation}$ can be monitored.

50. Surgical calibration device according to claim 46, wherein an operating time restriction device is provided to restrict the operating time $t_{operation}$ to a maximum time in a range of 1 second to 60 minutes.

51. Surgical calibration device according to claim 28, wherein the calibration unit comprises at least one inertial sensor.

52. Surgical calibration device according to claim 28, wherein:
the calibration unit and the at least one referencing unit respectively comprise at least one transmitting unit for transmitting measured values or changes of the position and/or orientation data of the calibration unit and the at least one referencing unit to the navigation system or to a detection device thereof during a navigation operation.

53. Surgical calibration device according to claim 28, wherein the navigation system comprises an evaluation unit, which is configured in such a manner that absolute position and/or orientation data can be calculated for the calibration unit and/or the at least one referencing unit from acceleration values measured by means of the at least one inertial sensor during a navigation operation.

54. Surgical calibration device according to claim 53, wherein:
the evaluation unit is configured and/or programmed in such a manner that position and/or orientation change data of the calibration unit and the at least one referencing unit can be calculated from the measured acceleration values in relation to the coordinate system, and
absolute position and/or orientation data of the calibration unit and the at least one referencing unit can be calculated from the calculated position and/or orientation change data in relation to the coordinate system.

55. Surgical calibration device according to claim 28, wherein:
an inertial sensor unit comprising the at least one inertial sensor is provided,
the inertial sensor unit comprises at least six acceleration sensors, with which accelerations acting on the calibration unit and/or the at least one referencing unit can be measured as a function of time in three mutually linearly independent directions and around three mutually linearly independent rotational axes.

56. Surgical calibration device according to claim 28, wherein at least one calibration gauge is provided, which has at least one calibration receiving means to at least partially receive the calibration unit in the defined position.

57. Surgical calibration device according to claim 56, wherein the at least one calibration gauge is arranged on the at least one referencing unit.

58. Surgical calibration device according to claim 56, wherein at least one calibration receiving means comprises a recess, which corresponds to a part of the calibration unit and into which the part of the calibration unit can be inserted in a positive arrangement.

59. Surgical calibration device according to claim 56, wherein the at least one calibration gauge is a one-, two- or three-dimensional calibration gauge for a position and/or orientation calibration of the at least one referencing unit and the calibration unit relative to one another.

60. Surgical calibration device according to claim 31, wherein the origin calibration gauge has at least one origin calibration receiving means for at least partially receiving the calibration unit in the origin calibration position.

61. Surgical calibration device according to claim 60, wherein the at least one origin calibration receiving means is a recess, which corresponds to a part of the calibration unit and into which the part of the calibration unit can be inserted in a positive arrangement.

62. Surgical calibration device according to claim 34, wherein the actuating element can be actuated manually.

63. Surgical calibration device according to claim 62, wherein the actuating element comprise a microswitch arranged on the at least one referencing unit.

* * * * *